US006124299A

United States Patent [19]
Baindur et al.

[11] Patent Number: 6,124,299
[45] Date of Patent: Sep. 26, 2000

[54] CALCITONIN MIMETICS

[75] Inventors: Nand Baindur, Edmonds, Wash.; Virender Labroo, Banglore, India; Steven Stroop; Stephanie Beigel, both of Seattle, Wash.; Theresa Martinez, Greenbank, Wash.; Charles R. Petrie, Woodinville, Wash.; Mark W. Orme, Seattle, Wash.; Patricia A. McKernan, Woodinville, Wash.; Emma E. Moore, Seattle, Wash.

[73] Assignee: ZymoGenetics, Inc., Seattle, Wash.

[21] Appl. No.: 09/028,085

[22] Filed: Feb. 23, 1998

Related U.S. Application Data

[60] Provisional application No. 60/038,971, Feb. 24, 1997, and provisional application No. 60/067,037, Dec. 1, 1997.

[51] Int. Cl.[7] ........................ A61K 31/495; A61K 31/55; A61K 31/415
[52] U.S. Cl. .................... 514/255.06; 514/250; 514/396; 514/211.08; 514/218
[58] Field of Search ............................... 514/255.06, 250, 514/227.8, 235.8, 252, 357, 360, 396, 211.08, 218

[56] References Cited

U.S. PATENT DOCUMENTS

| | | | |
|---|---|---|---|
| 4,153,794 | 5/1979 | Ishiguro et al. | 544/358 |
| 4,267,175 | 5/1981 | Watts | 514/218 |
| 4,420,482 | 12/1983 | Milani et al. | 514/255 |
| 5,250,528 | 10/1993 | Oku et al. | 514/252 |
| 5,286,728 | 2/1994 | Ferrini | 514/255 |
| 5,492,913 | 2/1996 | Wierzbicki et al. | 514/255 |
| 5,932,582 | 8/1999 | Young et al. | 514/255 |
| 5,952,306 | 9/1999 | Hartman et al. | 514/18 |

FOREIGN PATENT DOCUMENTS

| | | |
|---|---|---|
| 557030 | 10/1957 | Belgium . |
| 888.139 | 3/1981 | Belgium . |
| 0 028 031 A1 | 5/1981 | European Pat. Off. . |
| 0 318 235 A1 | 5/1989 | European Pat. Off. . |
| 0 436 734 A1 | 7/1991 | European Pat. Off. . |
| 0 617 027 A1 | 9/1994 | European Pat. Off. . |
| 0 733 627 A1 | 9/1996 | European Pat. Off. . |
| 1.031.571 | 6/1953 | France . |
| 832.436 | 11/1960 | France . |
| 1.297.718 | 5/1962 | France . |
| 823.137 | 5/1962 | France . |
| 1.303.080 | 7/1962 | France . |
| 2.113.942 | 6/1972 | France . |
| 2 291 757 | 6/1976 | France . |
| 2 353 540 | 12/1977 | France . |
| 2 377 377 | 8/1978 | France . |
| 2 387 955 | 11/1978 | France . |
| 874096 | 8/1961 | United Kingdom . |
| WO 90/13539 | 11/1990 | WIPO . |
| WO 96/31536 | 10/1996 | WIPO . |

OTHER PUBLICATIONS

McLeod, James F., et al. (1981) "Comparison of Inhibition of Bond Resorption and Escape with Calcitonin and Dibutyryl 3', 5' Cyclic Adenosine Monophosphate", *Endocrine Research Communications*, 8(1):49–59.

Wener, Jeffrey A., et al. (1972) "Escape from Inhibition of Resoprption in Cultures of Fetal Bone Treated with Calcitonin and Parathyroid Hormone", *Endocrinology*, 90:752–759.

Tashjian, Armen H., et al. (1978) "Calcitonin Binding Sites in Bone: Relationships to Biological Response and Escape", *Recent Progress in Hormone Research*, 34:285–303.

Mazzuli, Gian Franco, et al. (1990) "Effects of Salmon Calcitonin on the Bone Loss Induced by Ovariectomy", *Calcif Tissue Int* 47:209–214.

Wronski, T.J., et al. (1991) "Skeletal Effects of Calcitonin in Ovariectomized Rats", *Endocrinology* 129(4):2246–2250.

Lin, Herbert Y., et al. (1991) "Expression Cloning of an Adenylate Cyclase–Coupled Calcitonin Receptor", *Science*, 254:1022–1024.

Alvarez, Robert, et al. (1990) "A Single Column Method for the Assay of Adenylate Cyclase", *Analytical Biochemistry*, 187:98–103.

Steiner, Alton L., et al. (1972) "Radioimmunoassay for Cyclic Nucleotides", *The Journal of Biological Chemistry*, 247(4): 1106–1113.

Hayashi, T., et al. (1989) "Effect of $(Asu^{1,7})$–Eel Calcitonin on the Prevention of Osteoporosis Induced by Combination of Immobilization and Ovariectomy in the Rat", *Bone*, 10:25–28.

McSheehy, P.M.J., et al. (1995) "Pharmacologic Evaluation of the Calcitonin Analogue SB 205614 in Models of Osteoclastic Bone Resorption In Vitro and In Vivo: Comparison With Salmon Calcitonin and Elcatonin", *Bone*, 16(4):435–444.

Chemical Abstracts, vol. 66, No. 1, Jan. 2, 1967 Columbus, Ohio, US; abstract No. 1384, XP002068653 & L. Toldy et al.: Acta Chim. Acad. Sci. Hung, vol. 49, No. 3, 1996, pp. 265–285 & Database Registry Chemical Abstracts Service, Columbus, Ohio, US XP002069260 see RN 1062–48–2, 1104–59–2.

Chemical Abstracts, vol. 91, No. 5, Jul. 30, 1979, Columbus, Ohio, US; abstract No. 38433, XP002068654 & C. Farina et al.: Eur. J. Med. Chem.– Chim. Ther., vol. 14, No. 1, 1979, pp. 27–31, & Database Registry Chemical Abstracts Service, Columbus, Ohio, US XP002069261, see RN 70733–80–1.

(List continued on next page.)

Primary Examiner—Marianne M. Cintins
Assistant Examiner—Vickie Kim
Attorney, Agent, or Firm—Townsend and Townsend and Crew

[57] ABSTRACT

Compounds are described which act as calcitonin mimetics. These compounds are useful in the treatment of diseases which are associated with bone resorption. Included among the calcitonin mimetics of the present invention are substituted piperazines. The calcitonin mimetics of the present invention are also useful in libraries and in assays for the determination of calcitonin receptor activity.

11 Claims, 6 Drawing Sheets

OTHER PUBLICATIONS

Chemical Abstracts, vol. 69, No. 9, Aug. 26, 1968, Columbus, Ohio, US; abstract No. 36070, XP002068655 & T. Irikura et al.: J. Med. Chem. vol. 11, No. 4, 1968, pp. 801–804, & Database Registry Chemical Abstracts Service, Columbus, Ohio, US XP002069262, see RN 13754–35–3, 17698–20–3, 18907–63–6, 18907–64–7, 18907–66–9, 18940–64–2.

Chemical Abstracts, vol. 71, No. 13, Sep. 29, 1969, Columbus, Ohio, US; abstract No. 59406, XP002068657 & M. Nikolova, et al.: Farmatsiya., vol. 19, No. 2, 1969, pp. 31–37, & Database Registry Chemical Abstracts Service, Columbus, Ohio, US XP002069264, see RN 24646–78–4.

Chemical Abstracts, vol. 73, No. 5, Aug. 3, 1970, Columbus, Ohio, US; abstract No. 23815, XP002068658 & K. Lanyi, et al.: Pharmazie, vol. 25, No. 3, 1970, pp. 189–194, & Database Registry Chemical Abstracts Service, Columbus, Ohio, US XP002069265, see RN 4123–63–1, 4195–58–8.

Chemical Abstracts, vol. 53, No. 2, Jan. 25, 1960, Columbus, Ohio, US; abstract No. 21986f, XP002068659 & W.I. Ide et al.: J. Org. Chem., vol. 24, 1959, pp. 459–463, & Database Caold Chemical Abstracts Service, Columbus, Ohio, US XP002069267, see abstract 53:21986, RN 107778–34–7.

Chemical Abstracts, vol. 54, No. 11, Jun. 10, 1960, Columbus, Ohio, US; abstract No. 11035g, XP002068660 & L. Zhelyazkov, et al.: Farmatsiya., vol. 7, No. 6, 1957, pp. 17–19, & Database Caold Chemical Abstracts Service, Columbus, Ohio, US XP002069268, see abstract 54:11035, RN 111440–11–0.

Chemical Abstracts, vol. 54, No. 15, Aug. 10, 1960, Columbus, Ohio, US; abstract No. 15276, XP002068661 & J.F. Allen, et al.: J. Chem. Soc., 1960, pp. 1482–1487, & Database Caold Chemical Abstracts Service, Columbus, Ohio, US XP002069269, see abstract 54:15275, RN 108240–25–1.

Chemical Abstracts, vol. 57, No. 10, Nov. 12, 1962, Columbus, Ohio, US; abstract No. 12487i, XP002068662 & R. Dahlbom, et al.: Acta Chem. Scand., vol. 15, 1961, pp. 1367–1371, & Database Caold Chemical Abstracts Service, Columbus, Ohio, US XP002069270, see abstract 57:12488, RN 100321–37–7, 99711–97–4.

Chemical Abstracts, vol. 68, No. 19, May 6, 1968, Columbus, Ohio, US; abstract No. 87274, XP002068663 & R. B. Petigara et al.: J. Med. Chem., vol. 11, No. 2, 1968, pp. 332–336, & Database Registry Chemical Abstracts Service, Columbus, Ohio, US XP002069271, see RN 17766–62–0, 17766–61–9.

Chemical Abstracts, vol. 71, No. 11, Sep. 15, 1969, Columbus, Ohio, US; abstract No. 48267, XP002068664 & J.A. Ellard et al.: Trans. Ky. Acad. Sci., vol. 28, No. 1–4, 1967, pp. 20–32, & Database Registry Chemical Abstracts Service, Columbus, Ohio, US XP002069272, see RN 24773–78–2, 24773–79–3, 24773–80–6, 24773–81–7, 24773–82–8, 24773–83–9, 24773–85–1, 24773–86–2, 24773–87–3, 24773–90–8, 24773–11–6, etc.

Chemical Abstracts, vol. 75, No. 11, Sep. 13, 1971, Columbus, Ohio, US; abstract No. 76845, XP002068665 & JP 46 018 994 A (Kyorin Pharmaceutical Co., Ltd. & Database Registry Chemical Abstracts Service, Columbus, Ohio, US XP002069273, see RN 33107–13–0.

Chemical Abstracts, vol. 77, No. 1, Jul. 3, 1972, Columbus, Ohio, US; abstract No. 176, XP002068666 & L. Toldy et al.: Acta Chim., vol. 69, No. 2, 1971 & Database Registry Chemical Abstracts Service, Columbus, Ohio, US XP002069274, see RN 36993–54–1, 36993–56–3.

Chemical Abstracts, vol. 87, No. 5, Aug. 1, 1977, Columbus, Ohio, US; abstract No. 33511, XP002068667 & N. Ivanova et al.: Farmatsiya., vol. 26, No. 4, 1976 & Database Registry Chemical Abstracts Service, Columbus, Ohio, US XP002069275, see RN 48216–63–3.

Chemical Abstracts, vol. 88, No. 13, Mar. 27, 1978, Columbus, Ohio, US; abstract No. 89712, XP002068668 & JP 52 083 858 A (Takeda Chemical Industries, Ltd.)– & Database Registry Chemical Abstracts Service, Columbus, Ohio, US XP002069276, see RN 60261–53–2, 65663–33–4.

Chemical Abstracts, vol. 92, No. 23, Jun. 9, 1980, Columbus, Ohio, US; abstract No. 198426, XP002068669 & ES 479 627 A (Farmaceutici Geymonat Sud S.P.A.– & Database Registry Chemical Abstracts Service, Columbus, Ohio, US XP002069277, see RN 29231–91–2, 29231–92–3, 73535–69–0, 73535–70–3.

Chemical Abstracts, vol. 95, No. 11, Sep. 14, 1981, Columbus, Ohio, US; abstract No. 97732, XP002068670 & P. Avramova et al.: Prob. Farm., vol. 9, 1981, pp. 51–55, & Database Registry Chemical Abstracts Service, Columbus, Ohio, US XP002069278, see RN 78800–38–1.

Chemical Abstracts, vol. 95, No. 15, Oct. 12, 1981, Columbus, Ohio, US; abstract No. 132810, XP002068671 & S. Abuzar et al.: Indian J. Chem., Sect. B, vol. 20b, No. 3, 1981, pp. 230–233, –& Database Registry Chemical Abstracts Service, Columbus, Ohio, US XP002069279, see RN 78721–68–3, 78721–71–8.

Chemical Abstracts, vol. 101, No. 5, Jul. 30, 1984, Columbus, Ohio, US; abstract No. 32819, XP002068672 & A.–M. Scotto Di Tella et al.: Euro. J. Med. Chem.—Chim. Ther., vol. 19, No. 3, 1984, pp. 131–135, –& Database Registry Chemical Abstracts Service, Columbus, Ohio, US XP002069280, see RN 90754–70–4, 90774–21–3.

Chemical Abstracts, vol. 102, No. 21, May 27, 1985, Columbus, Ohio, US; abstract No. 185052, XP002068673 & S. Abuzar et al.: Pharmazie, vol. 39, No. 11, 1984, pp. 747–749, –& Database Registry Chemical Abstracts Service, Columbus, Ohio, US XP002069281, see RN 96103–51–4.

Chemical Abstracts, vol. 104, No. 19, May 12, 1986, Columbus, Ohio, US; abstract No. 168480, XP002068674 & JP 60 197 660 A (Mitsubishi Chemical Industries Co., Ltd.) –& Database Registry Chemical Abstracts Service, Columbus, Ohio, US XP002069282, see RN 101187–65–9.

Chemical Abstracts, vol. 104, No. 21, May 26, 1986, Columbus, Ohio, US; abstract No. 186377, XP002068675 & R.A. Lyon et al.: J. Med. Chem., vol. 29, No. 5, 1986, pp. 630–634 –& Database Registry Chemical Abstracts Service, Columbus, Ohio, US XP002069283, see RN 100940–14–5.

Chemical Abstracts, vol. 105, No. 13, Sep. 29, 1986, Columbus, Ohio, US; abstract No. 107935, XP002068676 & K. Nagarajan et al.: Indian J. Chem., Sect. B., vol. 24b, No. 9, 1985, pp. 934–939 –& Database Registry Chemical Abstracts Service, Columbus, Ohio, US XP002069284, see RN 104017–60–9.

Chemical Abstracts, vol. 108, No. 21, May 23, 1988, Columbus, Ohio, US; abstract No. 186530, XP002068677 & V.K. Agrawal et al.: Indian J. Chem., Sect. B., vol. 26b, No. 6, 1987, pp. 550–555 –& Database Registry Chemical Abstracts Service, Columbus, Ohio, US XP002069285, see RN 114260–09–2.

Chemical Abstracts, vol. 113, No. 23, Dec. 3, 1990, Columbus, Ohio, US; abstract No. 211780, XP002068678 & V. Valenta et al.: Collect. Czech. Chem. Commun., vol. 55, No. 5, 1990, pp. 1297–1310 –& Database Registry Chemical Abstracts Service, Columbus, Ohio, US XP002069286, see RN 130259–94–8, 130259–95–9, 130260–11–6, 130260–12–7.

Chemical Abstracts, vol. 113, No. 25, Dec. 17, 1990, Columbus, Ohio, US; abstract No. 231321, XP002068679 & V. Kmonicek et al.: Collect. Czech. Chem. Commun., vol. 55, No. 7, 1990, pp. 1817–1827 –& Database Registry Chemical Abstracts Service, Columbus, Ohio, US XP002069287, see RN 130564–54–4, 130564–55–5, 130564–57–7, 130564–58–8, 130564–59–9.

Chemical Abstracts, vol. 120, No. 11, Mar. 14, 1994, Columbus, Ohio, US; abstract No. 124467, XP002068680 & L. Xu et al.: Zhongguo Yaolixue Yu Dulixue Zazhi, vol. 7, No. 3, 1993, pp. 166–169 –& Database Registry Chemical Abstracts Service, Columbus, Ohio, US XP002069288, see RN 1257–19–8.

Chemical Abstracts, vol. 124, No. 15, Apr. 9, 1996, Columbus, Ohio, US; abstract No. 202178, XP002068681 & S. G. Abdel–Hamide et al.: Chem. Pap., vol. 49, No. 3, 1995, pp. 142–148 –& Database Registry Chemical Abstracts Service, Columbus, Ohio, US XP002069289, see RN 174152–77–3.

Chemical Abstracts, vol. 126, No. 1, Jan. 1, 1997, Columbus, Ohio, US; abstract No. 8072, XP002068682 & P. Zlatoidsky et al.: Eur. J. Med. Chem., vol. 31, No. 9, 1996, pp. 669–673 –& Database Registry Chemical Abstracts Service, Columbus, Ohio, US XP002069290, see RN 183591–50–6, 183591–62–0.

Chemical Abstracts, vol. 126, No. 7, Feb. 17, 1997, Columbus, Ohio, US; abstract No. 89335, XP002068683 see abstract: RN 185547–11–9 & P. Zlatoidsky et al.: Eur. J. Med. Chem., vol. 31, No. 11, 1996, pp. 895–899 –& Database Registry Chemical Abstracts Service, Columbus, Ohio, US XP002069291, see RN 185547–11–9.

CALCITONIN MIMETICS

CROSS REFERENCE TO RELATED APPLICATIONS

This application claims the benefit of provisional patent application no. 60/038,971, filed on Feb. 24, 1997, herein incorporated by reference, and provisional patent application no. 60/067,037, filed on Dec. 1, 1997, herein incorporated by reference.

BACKGROUND OF THE INVENTION

Bone is a dynamic tissue, and homeostasis in the adult skeleton requires a balance between bone resorption and bone formation. Osteoclasts and osteoblasts play a key role in this balance, with osteoclasts initiating bone resorption and osteoblasts synthesizing and depositing new bone matrix. Imbalances in bone homeostasis are associated with such conditions as osteoporosis, Paget's disease, and hyperparathyroidism.

The activities of osteoclasts and osteoblasts are regulated by complex interactions between systemic hormones and the local production of growth factors and cytokines. Calcitonin, a peptide hormone secreted by the thyroid and thymus of mammals, plays an important role in maintaining bone homeostasis. Calcitonin inhibits bone resorption through binding and activation of a specific calcitonin receptor on osteoclasts (*The Calcitonins—Physiology and Pharmacology*, Azria (ed.), Karger, Basel, Su., 1989), with a resultant decrease in the amount of calcium released by bone into the serum. This inhibition of bone resorption has been exploited, for instance, by using calcitonin as a treatment for osteoporosis, a disease characterized by a decrease in the skeletal mass often resulting in debilitating and painful fractures. Calcitonin is also used in the treatment of Paget's disease where it provides rapid relief from bone pain, which is frequently the primary symptom associated with this disease. This analgesic effect has also been demonstrated in patients with osteoporosis or metastatic bone disease and has been reported to relieve pain associated with diabetic neuropathy, cancer, migraine and post-hysterectomy. Reduction in bone pain occurs before the reduction of bone resorption.

Salmon calcitonin has been shown to be considerably more effective in arresting bone resorption than human forms of calcitonin. Several hypotheses have been offered to explain this observation: 1) salmon calcitonin is more resistant to degradation; 2) salmon calcitonin has a lower metabolic clearance rate (MCR); and 3) salmon calcitonin may have a slightly different conformation, resulting in a higher affinity for bone receptor sites.

Despite the advantages associated with the use of salmon calcitonin in humans, there are also disadvantages. For treatment of osteoporosis, for instance, the average cost can exceed $75 a week and involve daily prophylactic administration for 5 or more years. In the United States, calcitonin must be administered by injection, and since the disease indications for this drug are not usually life threatening, patient compliance can be low.

Furthermore, resistance to calcitonin therapy may occur with long-term use. What triggers this resistance or "escape phenomenon" is unknown (see page 1093, *Principles of Bone Biology*, Bilezikian et al., (eds.) Academic Press, NY; Raisz et al., *Am. J. Med.* 43:684–90 (1967); McLeod & Raisz, *Endocrine Res. Comm.* 8:49–59 (1981); Wener et al., *Endocrinology* 90:752–9 (1972); and Tashjian et al., *Recent Prog. Horm. Res.* 34:285–303 (1978)). Use of calcitonin mimetics, either in place of native calcitonins or in rotation with native calcitonins, would help avoid resistance to such treatment during long-term use. In addition, some patients develop antibodies to non-human calcitonin, calcitonin mimetics would be useful for such patients.

What is needed in the art are alternative methods of inhibiting bone resorption. Surprisingly, the present invention fulfills these and other needs.

SUMMARY OF THE INVENTION

The present invention provides isolated compounds that are calcitonin mimetics. As used herein, the term "calcitonin mimetic" refers to a compound with the ability to mimic the effects generated by calcitonin's interaction with its receptor and, by such interaction, stimulate G-protein-mediated activation by adenylate cyclase. As a result, these compounds are useful in the treatment of diseases which are mediated by calcitonin. Included among the calcitonin mimetics of the present invention are piperazine derivatives in which each of the nitrogens in the piperazine ring are alkylated or acylated with substituted aryl groups.

In view of the present discoveries, the invention provides methods for the inhibition of bone resorption which is useful for the treatment of osteoporosis, Paget's disease, hyperparathyroidism, osteomalacia, periodontal defects (bone loss prevention), hypercalcemia of malignancy, idiopathic hypercalcemia of infancy and other conditions. The calcitonin mimetics can also be used to inhibit gastric secretion in the treatment of acute pancreatitis and gastrointestinal disorders, and as analgesics, in particular for bone pain. The calcitonin mimetics described herein may be used alone or in combination with other therapeutic agents.

In other aspects, the present invention provides libraries of calcitonin mimetics which are attached to a solid support, or attached to multiple solid supports. The present invention further provides methods of preparing the libraries as well as methods of screening the libraries to determine relative binding efficiencies of the attached piperazine derivatives to the calcitonin receptor.

DETAILED DESCRIPTION OF THE INVENTION

I. Abbreviations

Figure 1:
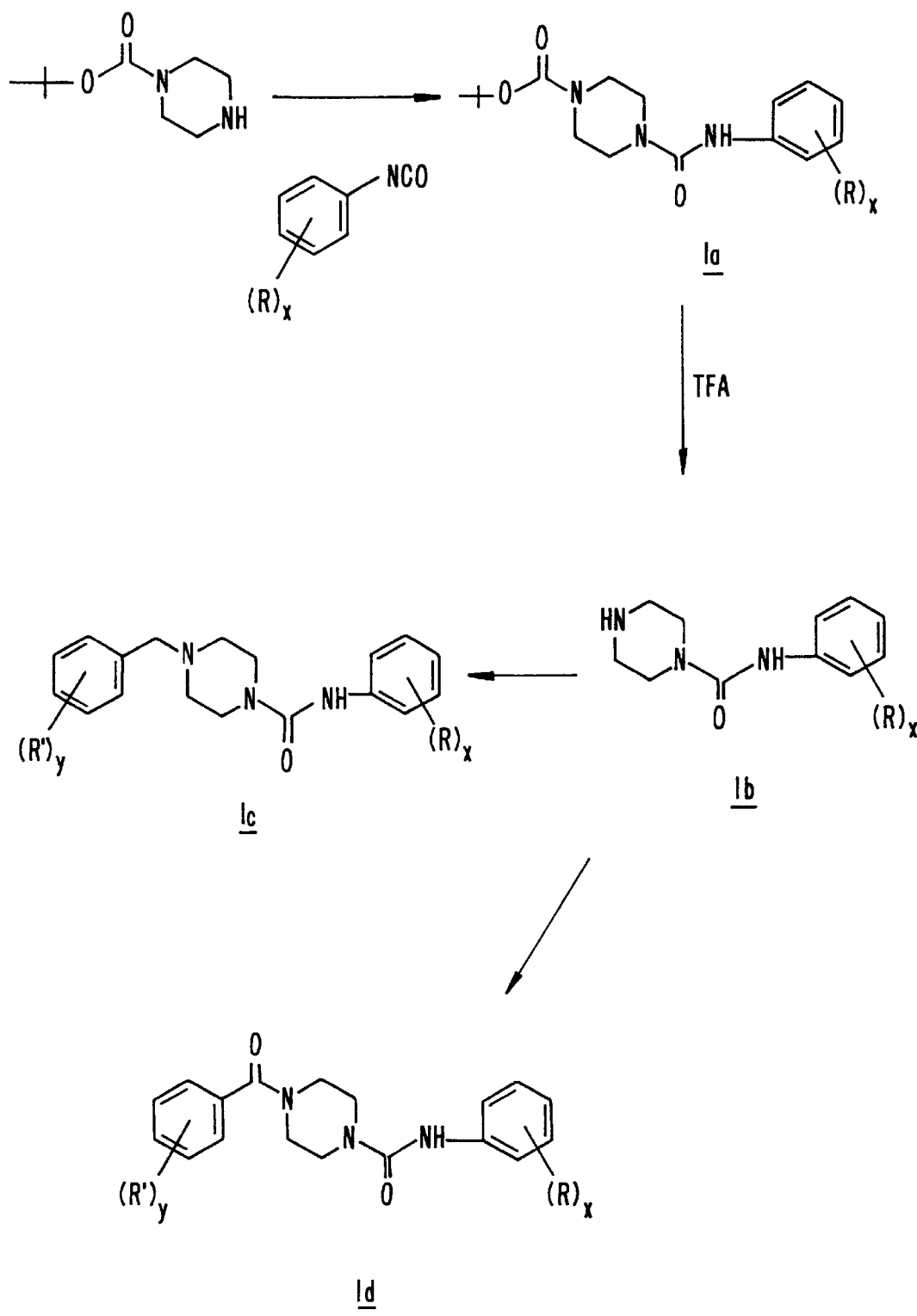
FIGS. 1 and 2 are synthesis schemes for the preparation of compounds of the present invention.

The following abbreviations are used herein: Boc, t-butoxycarbonyl; DCM, dichloromethane; DME, dimethoxyethane; DMF, dimethylformamide; EtOAc, ethyl acetate; Fmoc, fluorenylmethoxycarbonyl; TFA, trifluoroacetic acid.

II. Calcitonin Mimetics

The calcitonin mimetics that are useful in the present invention are those compounds with the ability to mimic the interaction of calcitonin with its receptor and, by such mimicry to stimulate G-protein-mediated activation of adenylate cyclase. These mimetics are represented by the general formula:

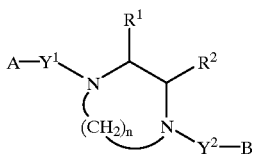

(I)

In this formula, the letters A and B each independently represent an aryl group, a substituted aryl group, a carbocyclic ring, a substituted carbocyclic ring, a heterocyclic ring, a substituted heterocyclic ring, or combinations thereof. The combinations can be fused or covalently linked. Examples of carbocyclic and heterocyclic groups include cyclohexyl, cyclohexenyl, piperazinyl, pyrazinyl, morpholinyl, imidazolyl, triazolyl and thiazolyl. As noted above, each of A and B can be an aryl group. The term "aryl" refers to an aromatic substituent which may be a single ring or multiple rings which are fused together, linked covalently or linked to a common group such as an ethylene or methylene moiety. The aromatic rings may each contain heteroatoms. Examples of aryl groups include phenyl, naphthyl, biphenyl, diphenylmethyl, 2,2-diphenyl-1-ethyl, thienyl, pyridyl and quinoxalyl. Additionally, the aryl groups may be attached to other parts of the molecule at any position on the aryl radical which would otherwise be occupied by a hydrogen atom (such as, for example, 2-pyridyl, 3-pyridyl and 4-pyridyl).

The aryl groups, along with any carbocyclic or heterocyclic groups may also be optionally substituted. The substituents are typically halogen, haloalkyl, hydroxy, aryloxy, benzyloxy, alkoxy, haloalkoxy, amino, monoalkylamino, dialkylamino, acyloxy, acyl, alkyl or additional aryl groups. The term "alkyl," as used herein, refers to a saturated hydrocarbon radical which may be straight-chain or branched-chain (for example, ethyl, isopropyl, or t-amyl), or cyclic (for example cyclobutyl, cyclopropyl or cyclopentyl). Preferred alkyl groups are those containing 1 to 6 carbon atoms. All numerical ranges in this specification and claims are intended to be inclusive of their upper and lower limits. The term "alkoxy" refers to an alkyl radical as described above which also bears an oxygen substituent which is capable of covalent attachment to another hydrocarbon radical (such as, for example, methoxy, ethoxy and t-butoxy).

The symbols $R^1$ and $R^2$ are each independently hydrogen or alkyl groups having from 1 to 6 carbon atoms. In some embodiments $R^1$ and $R^2$ can be joined together to form a ring which is a four-, five-, six- or seven-member ring, saturated or unsaturated. For those embodiments in which the ring is unsaturated, the ring can be an aromatic ring (e.g., phenyl or naphthyl) or a heteroaromatic ring (e.g., pyridyl, thienyl, imidazolyl).

The symbols $Y^1$ and $Y^2$ each independently represent a bond or a divalent radical that is —$CH_2$—, —NHC(O)—, —NRC(O)—, —NHC(S)—, —NRC(S)—, —NHC(=NH)—, —OC(O)—, —C(O)—, or —C(S)—, in which R is a lower alkyl group of from one to six carbon atoms. In preferred embodiments, $Y^2$ represents a divalent radical which is a carbonyl, thiocarbonyl or methylene, represented as —C(O)—, —C(S)— or —$CH_2$—, respectively. In other preferred embodiments, $Y^1$ is —NHC(O)—, —NRC(O)—, —C(O)—, or —C(S)—.

The letter n represents an integer of from zero to four.

In one group of preferred embodiments, the calcitonin mimetics are piperazine-based compounds which are represented by the formula:

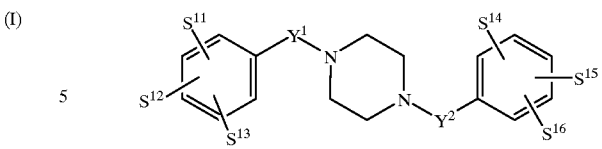

In this formula, the symbols $Y^1$ and $Y^2$ have the meaning provided above. The symbols $S^{11}$, $S^{12}$, $S^{13}$, $S^{14}$, $S^{15}$, and $S^{16}$ each independently represent a substituent on the attached aromatic ring which is hydrogen, halogen, haloalkyl, hydroxy, aryloxy, benzyloxy, alkoxy, haloalkoxy, amino, monoalkylamino, dialkylamino, acyloxy, acyl, alkyl and aryl. In particularly preferred embodiments, $Y^1$ is —NHC(O)— or —$CH_2$—, $Y^2$ is —$CH_2$—, and $S^{11}$, $S^{12}$, $S^{13}$, $S^{14}$, $S^{15}$, and $S^{16}$ each independently represent hydrogen, halogen, haloalkyl, hydroxy, alkoxy, haloalkoxy, amino, monoalkylamino or dialkylamino. In certain preferred embodiments, at least one and preferably at least two of the substituents on each aromatic ring are other than hydrogen. Most preferably, the substituents are halogen, trifluoromethyl, hydroxy and methoxy.

Figure 2:
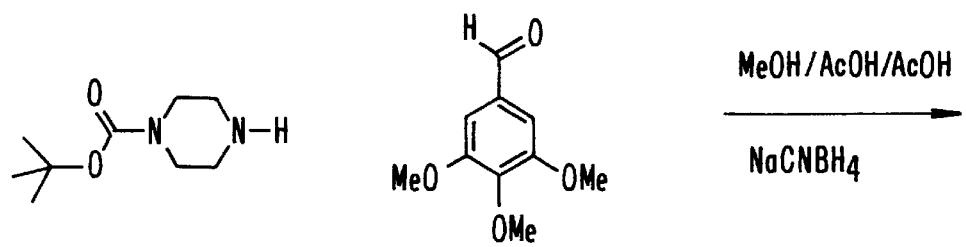
Figure 2:
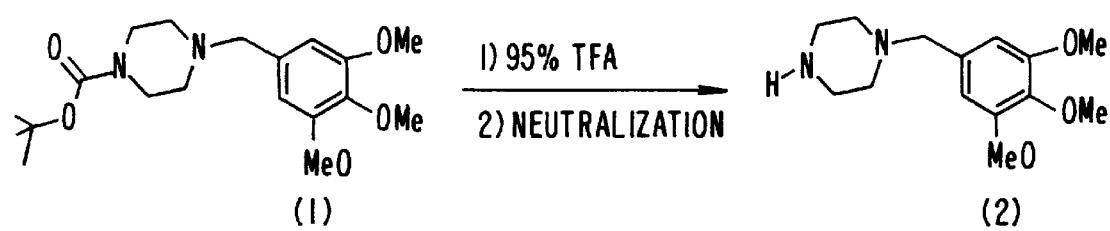
Figure 2:
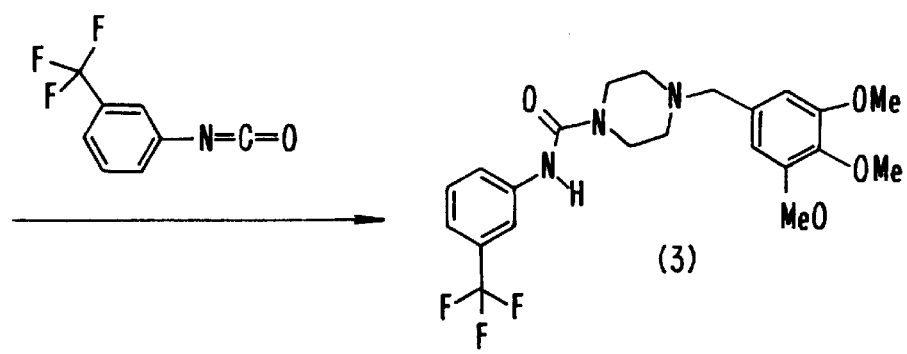

The calcitonin mimetics used in the present invention can be prepared by standard synthetic methods which are known to those of skill in the art. A general synthetic scheme directed to piperazine derivatives is provided in FIG. 1. Thus, a monoprotected piperazine (e.g., t-BOC-piperazine) can be treated with an aryl isocyanate to provide a urea 1a. Removal of the protecting group from 1a provides 1b which can be alkylated or acylated according to conventional methods with, for example, a substituted benzyl halide or a substituted benzoyl chloride to provide 1c and 1d, respectively. Alternatively, t-Boc piperazine can be alkylated using a reductive amination route as illustrated in FIG. 2. Following the reductive alkylation with, for example, an aromatic aldehyde, the protecting group can be removed and the remaining piperazine nitrogen can be acylated with an aryl or alkyl isocyanate. Still other preparative methods can be employed which are analogous to those described for the preparation of related compounds in U.S. Pat. Nos. 5,286,728 and 5,384,319, the disclosures of which are incorporated herein by reference.

In another synthetic methodology directed toward the calcitonin mimetics, a suitably substituted hydroxybenzaldehyde is first linked to a solid support, such as Wang resin. The free aldehyde group is then subjected to reductive alkylation employing a monoprotected diamine, such as BOC-piperazine. The protecting group is then removed and the resin-bound compound is acylated with a variety of reagents, such as carboxylic acids, isocyanates, isothiocyanates or sulfonyl halides. The mono-protected diamines, including piperazines, are either commercially available or can be prepared by a variety of methods known to those skilled in the art of organic synthesis. In one approach, 4-hydroxy-3-methoxybenzaldehyde is attached to Wang resin by Mitsonobu alkylation employing triphenylphosphine and diethylazodicarboxylate. The free aldehyde group of the resin-bound compound is then reductively alkylated with BOC-piperazine employing borane-pyridine complex. The BOC group is then selectively removed with 10% TFA/DCM and the free nitrogen is then acylated with arylisocyanates. Cleavage of the resulting compound is then effected by standard methods, for example using 50% TFA/DCM for 30 minutes. One of skill in the art will recognize that a number of alternative procedures exist for the preparation of the present compounds, including reversing the order of synthesis on the resin, using other reagents for the acylations and couplings which are described in, for example, March, *Advanced Organic Chemistry*, Fourth Edition, Wiley-Interscience, NY, (1992), incorporated herein by reference.

III. In Vivo Uses

The compounds of the invention can be administered to warm blooded animals, including humans, to mimic the interaction of calcitonin with its receptor in vivo. Within one aspect, calcitonin mimetics of the present invention are contemplated to be advantageous for use in therapeutic defects for which calcitonin is useful. In particular, the calcitonin mimetics are useful for the regulation of bone metabolism and reduction of serum calcium. The calcitonin mimetics of the invention can be administered to warm blooded animals, including humans, to mimic the interaction of calcitonin with its receptor in vivo. Thus, the present invention encompasses methods for therapeutic treatment of bone-related disorders. Such bone-related disorders include, but are not limited to, osteoporosis, Paget's Disease, hyperparathyroidism, osteomalacia, periodontal defects (bone loss), hypercalcemia of malignancy, idiopathic hypercalcemia of infancy, and other related conditions. Calcitonin mimetics are also contemplated to be advantageous as analgesics, in particular for relief of bone pain. Calcitonin mimetics are further contemplated to be advantageous in inhibiting bone resorption. The calcitonin mimetics of the present invention can also be used to inhibit gastric secretion in the treatment of acute pancreatitis and gastrointestinal disorders. The methods of the present invention may be used to treat these conditions in their acute or chronic stages.

Pharmaceutically or therapeutically effective amounts of calcitonin mimetics of the present invention can be formulated with pharmaceutically or therapeutically acceptable carriers for parenteral, oral, nasal, rectal, topical, transdermal administration or the like, according to conventional methods. Formulations may further include one or more diluents, fillers, emulsifiers, preservatives, buffers, excipients, and the like, and maybe provided in such forms as liquids, powders, emulsions, suppositories, liposomes, transdermal patches and tablets, for example. Slow or extended-release delivery systems, including any of a number of biopolymers (biological-based systems), systems employing liposomes, and polymeric delivery systems, can also be utilized with the compositions described herein to provide a continuous or long-term source of the calcitonin mimetic. Such slow release systems are applicable to formulations, for example, for oral, topical and parenteral use. The term "pharmaceutically or therapeutically acceptable carrier" refers to a carrier medium which does not interfere with the effectiveness of the biological activity of the active ingredients and which is not toxic to the host or patient. One skilled in the art may formulate the compounds of the present invention in an appropriate manner, and in accordance with accepted practices, such as those disclosed in *Remington's Pharmaceutical Sciences*, Gennaro (ed.), Mack Publishing Co., Easton, Pa. (1990) (which is incorporated herein by reference in its entirety). Preferably such compounds would be administered orally or parenterally.

As used herein, a "pharmaceutically or therapeutically effective amount" of such a calcitonin mimetic is an amount sufficient to induce a desired biological result. The result can be alleviation of the signs, symptoms, or causes of a disease, or any other desired alteration of a biological system. For example, an effective amount of a calcitonin mimetic is that which provides either subject relief of symptoms or an objectively identifiable improvement as noted by the clinician or other qualified observer. In particular, such an effective amount of a calcitonin mimetic results in reduction in serum calcium, inhibition of bone resorption, inhibition of gastric secretion or other beneficial effect. Effective amounts of the calcitonin mimetics can vary widely depending on the disease or symptom to be treated. The amount of the mimetic to be administered, and its concentration in the formulations, depends upon the vehicle selected, route of administration, the potency of the particular mimetic, the clinical condition of the patient, the side effects and the stability of the compound in the formulation. Thus, the clinician will employ the appropriate preparation containing the appropriate concentration in the formulation, as well as the amount of formulation administered, depending upon clinical experience with the patient in question or with similar patients. Such amounts will depend, in part, on the particular condition to be treated, age, weight, and general health of the patient, and other factors evident to those skilled in the art. Typically a dose will be in the range of 0.1–100 mg/kg of subject. Preferably 0.5–50 mg/kg. Doses for specific compounds may be determined from in vitro or ex vivo studies on experimental animals. Concentrations of compounds found to be effective in vitro or ex vivo provide guidance for animal studies, wherein doses are calculated to provide similar concentrations at the site of action. Doses determined to be effective in experimental animals are generally predictive of doses in humans within one order of magnitude.

Well established animal models are available to test in vivo efficacy of calcitonin mimetics. For example, the hypocalcemic rat model can be used to determine the effect of synthetic calcitonin mimetics on serum calcium, and the ovariectomized rat or mouse can be used as a model system for osteoporosis. Bone changes seen in these models and in humans during the early stages of estrogen deficiency are qualitatively similar. Calcitonin has been shown to be an effective agent for the prevention of bone loss in ovariectomized humans and also in rats (Mazzuoli et al., *Calcif. Tissue Int.* 47:209–14 (1990); Wrongski et al., *Endocrinology* 129:2246–50 (1991)).

Preferably the compositions are presented for administration in unit dosage forms. The term "unit dosage form" refers to physically discrete units suitable as unitary doses for human subjects and animals, each unit containing a predetermined quantity of active material calculated to produce a desired pharmaceutical effect in association with the required pharmaceutical diluent, carrier or vehicle. Examples of unit dosage forms include vials, ampules, tablets, caplets, pills, powders, granules, eyedrops, oral or ocular solutions or suspensions, ocular ointments, and oil-in-water emulsions. Means of preparation, formulation and administration are known to those of skill; see generally *Remington's Pharmaceutical Science* 15$^{th}$ ed., Mack Publishing Co., Easton, Pa. (1990).

The dosages of the present compounds used to practice the invention include dosages effective to result in the desired effects. Estimation of appropriate dosages effective for the individual patient is well within the skill of the ordinary prescribing physician or other appropriate health care practitioner. As a guide, the clinician can use conventionally available advice from a source such as the *Physician's Desk Reference*, 48$^{th}$ Edition, Medical Economics Data Production Co., Montvale, N.J. 07645-1742 (1994).

IV. Libraries of Calcitonin Mimetics

In another aspect, the present invention provides libraries of calcitonin mimetics, each member of the library having the formula:

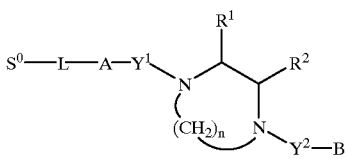

in which $S^0$ represents a solid support, L represents a bond, spacer or a linking group, and A, B, $R^1$, $R^2$, $Y^1$, $Y^2$ and n represent the groups described above for the compounds of formula I.

The solid support may be biological, nonbiological, organic, inorganic, or a combination of any of these, existing as particles, strands, precipitates, gels, sheets, tubing, spheres, containers, capillaries, pads, slices, films, plates, slides, etc. The solid support may be flat but may take on alternative surface configurations. For example, the solid support may contain raised or depressed regions on which synthesis takes place. In some embodiments, the solid support will be chosen to provide appropriate light-absorbing characteristics. For example, the support may be a polymerized Langmuir Blodgett film, functionalized glass, Si, Ge, GaAs, GaP, $SiO_2$, $SiN_4$, modified silicon, or any one of a variety of gels or polymers such as (poly) tetrafluoroethylene, (poly)vinylidendifluoride, polystyrene, polycarbonate, or combinations thereof. Other suitable solid support materials will be readily apparent to those of skill in the art. In another embodiment, the surface of the solid support will contain reactive groups, which could be carboxyl, amino, hydroxyl, thiol, or the like. Preferred solid supports are organic polymer beads.

Attached to the solid support is an optional spacer or linking group, L. The spacer molecules are preferably of sufficient length to permit the receptor ligands in the completed member of the library to interact freely with receptors exposed to the library. The spacers, when present, are typically 6–50 atoms long to provide sufficient exposure for the attached receptor ligand. The spacer or linking group, L, is comprised of a surface attaching portion and a ligand attaching site. The surface attaching portion is that part of L which is directly attached to the solid support. This portion can be attached to the solid support via carbon—carbon bonds using, for example, supports having (poly) trifluorochloroethylene surfaces, or preferably, by siloxane bonds (using, for example, glass or silicon oxide as the solid support). Siloxane bonds with the surface of the support are formed in one embodiment via reactions of surface attaching portions bearing trichlorosilyl or trialkoxysilyl groups. The spacer or linking group will also have a ligand attaching site. Functional groups which are suitable for attachment to a receptor ligand include amines, hydroxyl, thiol, and carboxyl. The surface attaching portion and the ligand attaching site can be separated by a variety of groups including alkylene groups (e.g., ethylene, propylene, butylene, etc.), ethylene glycol oligomers containing 2–14 monomer units, diamines, diacids, amino acids, peptides, or combinations thereof. Additionally, this portion of the spacer can be selected based upon its hydrophilic/hydrophobic properties to improve presentation of the ligands to the receptors. This portion of L can be constructed of polyethyleneglycols, alkylene, polyalcohol, polyester, polyamine, polyphosphodiester and combinations thereof.

Attached to the distal end of L is a receptor ligand, also referred to herein as a calcitonin mimetic. The ligands which are attached to preselected regions of a solid support, or alternatively to individual solid supports are each independently compounds of formula (I) which have been described above. These compounds are each attached to a linking group or spacer, typically through a hydroxyl functionality (—OH) present on the "A" ring of the mimetic.

The library can have virtually any number of different members, and will be limited only by the number or variety of compounds desired to be screened in a given application and by the synthetic capabilities of the practitioner. In one group of embodiments, the library will have from 2 up to 100 members. In other groups of embodiments, the library will have between 100 and 10000 members, and between 10000 and 1000000 members, preferably on a solid support. In preferred embodiments, the library will have a density of more than 100 members at known locations per $cm^2$, preferably more than 1000 per $cm^2$, more preferably more than 10,000 per $cm^2$.

Preparation of the Libraries

The libraries of the present invention can be prepared using a variety of solid phase techniques which are known to those of skill in the art. A general description of the preparation is provided with reference to FIG. 3.

Figure 3:
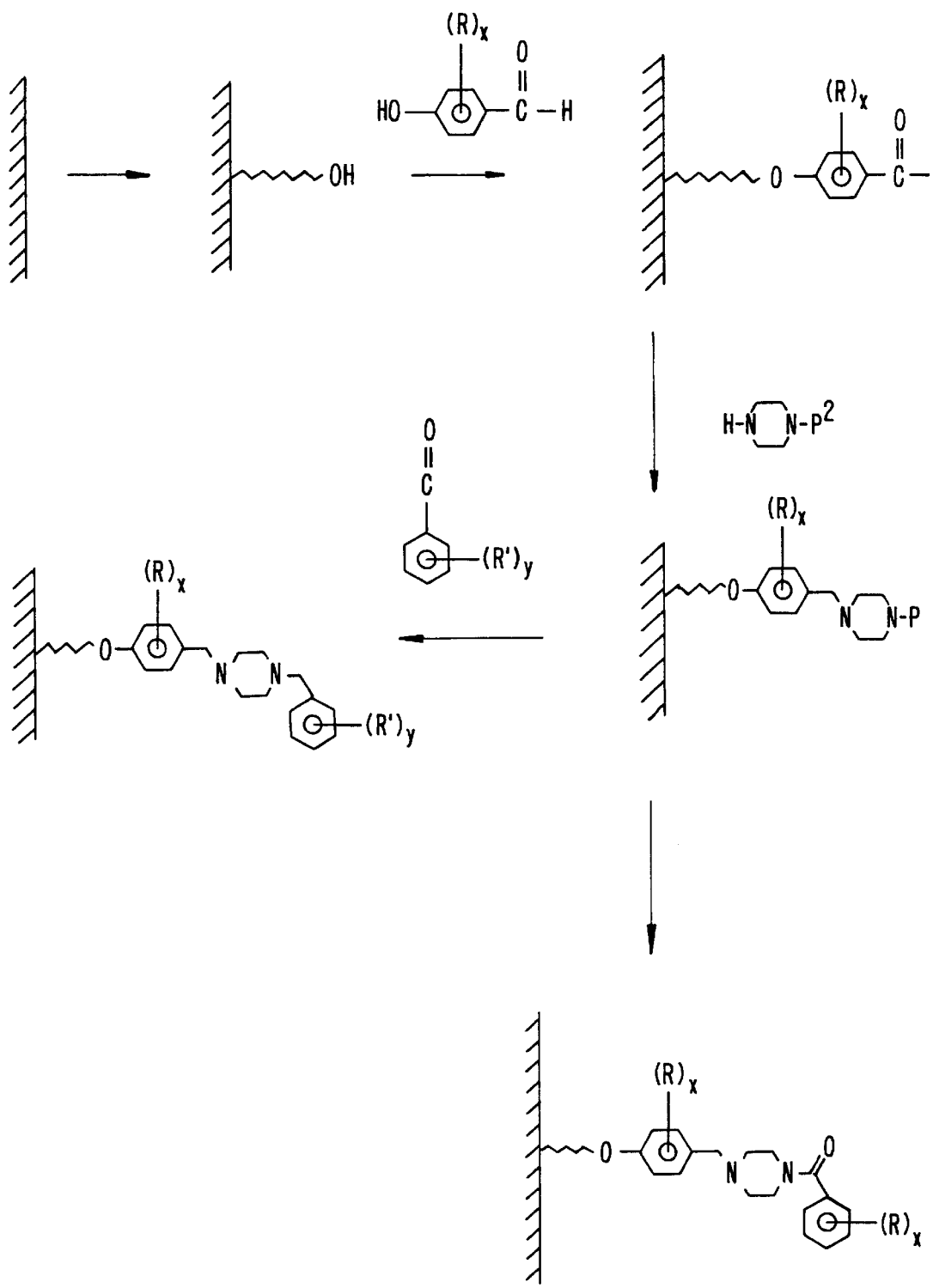
FIG. 3 shows one approach to the solid phase synthesis of compounds of the present invention, whether individually or as a member of a library.

As shown in FIG. 3 (illustrating only a single compound synthesis), a linking group is attached to a solid support to provide a derivatized solid support having a plurality of available ligand attaching sites. To the sites in the derivatized support is attached a suitably substituted hydroxybenzaldehyde. The free aldehyde group is then subjected to reductive alkylation employing a monoprotected diamine, such as BOC-piperazine. The protecting group is then removed and the resin-bound compound is acylated with a variety of reagents, such as carboxylic acids, isocyanates, isothiocyanates or sulfonyl halides. The mono-protected diamines, including piperazines, are either commercially available or can be prepared by a variety of methods known to those skilled in the art of organic synthesis. In one group of embodiments, each chemically distinct member of the library will be synthesized on a separate solid support.

A more thorough discussion of the various solid phase techniques can be found in the patents and publications provided below.

Libraries on a Substrate

Light-Directed Methods

For those embodiments using a single solid support, the libraries of receptor ligands of the present invention can be formed using, for example, "light directed" methods (which are one technique in a family of methods known as VLSIPS™ methods). These methods are described in U.S. Pat. No. 5,143,854, incorporated by reference.

Flow Channel or Spotting Methods

Additional methods applicable to library synthesis on a single substrate are described in U.S. Pat. No. 5,384,261, incorporated herein by reference for all purposes. In the methods disclosed in therein, reagents are delivered to the substrate by either (1) flowing within a channel defined on predefined regions or (2) "spotting" on predefined regions. However, other approaches, as well as combinations of spotting and flowing, may be employed. In each instance, certain activated regions of the substrate are mechanically separated from other regions when the monomer solutions are delivered to the various reaction sites.

Pin-Based Methods

Another method which is useful for the preparation of compounds and libraries of the present invention involves "pin based synthesis." This method is described in detail in U.S. Pat. No. 5,288,514, incorporated herein by reference. The method utilizes a substrate having a plurality of pins or other extensions. The pins are each inserted simultaneously into individual reagent containers in a tray. In a common embodiment, an array of 96 pins/containers is utilized.

Bead Based Methods

Yet another method which is useful for synthesis of compounds and libraries of the present invention involves "bead based synthesis." A general approach for bead based synthesis is described in published PCT/US93/04145 (filed Apr. 28, 1993), the disclosure of which is incorporated herein by reference.

In one group of preferred embodiments, a library of calcitonin mimetics is prepared using bead-based synthesis. In brief, beads are suitably modified with a spacer or linking group, for example, aminoalkyltriethoxysilane, to provide beads having amino groups as synthesis initiation sites. Linking groups are attached to the amino groups to provide derivatized beads having a general formula:

in which $S^0$ is the solid support and L is a combination of spacer (aminoalkylsilane) and linking group. Attached to the linking group is the "A" ring (e.g., an aromatic ring) having a functionality which is suitable for continued construction of the ligand. In some embodiments, the functionality is protected as, for example, its FMOC carbamate. One of skill in the art will understand that a number of protecting groups are available for use in preparing the libraries of the present invention. As used herein, the term "protecting group" refers to any of the groups which are designed to block one reactive site in a molecule while a chemical reaction is carried out at another reactive site. More particularly, the protecting groups used herein can be any of those groups described in Greene, et al., *Protective Groups In Organic Chemistry*, 2nd Ed., John Wiley & Sons, New York, N.Y. (1991), incorporated herein by reference. The proper selection of protecting groups for a particular synthesis will be governed by the overall methods employed in the synthesis. For example, in "light-directed" synthesis, discussed below, the protecting groups will be photolabile protecting groups such as 3,4-dimethoxy-6-nitrobenzyl carbamate, and those disclosed in published PCT/US93/10162 (filed Oct. 22, 1993), incorporated herein by reference. In other methods, protecting groups may be removed by chemical methods and include groups such as Fmoc, Dmt and others known to those of skill in the art. Selection of the protecting groups will depend on conditions for their selective removal as well as their compatibility with other features of the library members which are being synthesized. For example, when photolabile functionality is present, the protecting groups should be selectively removable by chemical means (i.e., the use of dilute acid or base, or hydrogenolysis). Thus, Fmoc and Boc are only two examples of selectively removable protecting groups. Following attachment of a suitably protected "A" ring to the linker on the solid support, the "A" ring can be selectively derivatized. This derivatization is achieved by first removing the protecting group and attaching the desired nitrogen-containing heterocycle to the synthesis site. Next, the second protecting group on the heterocyclic portion is removed and the free amine of appropriate building blocks is covalently attached to that site. The diversity of, for example, piperazine derivatives which can be synthesized by this route is a result of the combinatorial array of building blocks which can be used. For example, the building blocks can be selected from compounds having a variety of functional groups, including amino acids and peptides, carboxylic acids, and isocyanates.

Only those compounds which retain calcitonin-like activity, as assayed by a CRE-luciferase assay, for example, are within the scope of this invention. The calcitonin receptor is a member of the G-protein receptor family and transduces signal via activation of adenylate cyclase, leading to elevation of cellular cAMP levels (Lin et al., *Science* 254:1022–24 (1991)). This assay system exploits the receptor's ability to detect other molecules, not calcitonin, that are able to stimulate the calcitonin receptor and initiate signal transduction.

Receptor activation can be detected by: (1) measurement of adenylate cyclase activity (Salomon et al., *Anal. Biochem.* 58:541–48 (1974); Alvarez & Daniels, *Anal. Biochem.* 187:98–103 (1990)); (2) measurement of change in intracellular cAMP levels using conventional radioimmunoassay methods (Steiner et al., *J. Biol. Chem.* 247:1106–13 (1972); Harper & Brooker, *J. Cyc. Nucl. Res.* 1:207–18 (1975)); or (3) use of a cAMP scintillation proximity assay (SPA) method (Amersham Corp., Arlington Heights, Ill.). While these methods provide sensitivity and accuracy, they involve considerable sample processing prior to assay, are time consuming, may involve the use of radioisotopes, and would be cumbersome for large scale screening assays.

An alternative assay system (described in WO96/31536 which is incorporated herein in its entirety) involves selection of substances that are able to induce expression of a cyclic AMP response element (CRE)-luciferase reporter gene, as a consequence of elevated cAMP levels, in cells expressing a calcitonin receptor, but not in cells lacking calcitonin receptor expression. Such cells could include, for example, Boris/KS10-3 (expressing hamster calcitonin receptor and a CRE-luciferase reporter gene in baby hamster kidney cells (BHK 570 cells)) or Hollex 1 (expressing human calcitonin receptor and a CRE-luciferase reporter gene in BHK cells, as described in WO96/31536) or KZ10-20-48/pLJ6-4-25, which expresses the human glucagon receptor and a CRE-luciferase reporter gene in BHK cells. The human glucagon receptor is another member of the G-protein-coupled receptor is another member of the G-protein-coupled receptor family that transduces signal through adenylate cyclase-mediated elevation of cAMP.

This CRE-luciferase assay measures the end result of a multi-step signal transduction pathway triggered when a calcitonin mimetic stimulates the G-coupled calcitonin receptor. The complexity of this pathway provides multiple mechanisms for induction of luciferase transcription at points that are downstream of the calcitonin receptor, and therefore may not be calcitonin receptor-specific (e.g., forskolin's direct activation of adenylate cyclase). Any response triggered by non-specific inducers is eliminated by counter screening using the calcitonin receptor-negative cell lines described above.

The foregoing description and the following examples are offered primarily for illustration and not as limitations. It will be readily apparent to those of ordinary skill in the art that the operating conditions, materials, procedural steps and other parameters of the system described herein may be further modified or substituted in various ways without departing from the spirit and scope of the invention.

EXAMPLES

Example 1

1.1 Synthesis of Mimetic 3

This example illustrates the synthesis of a calcitonin mimetic 3 below, from commercially available starting materials using the scheme outlined in FIG. 2.

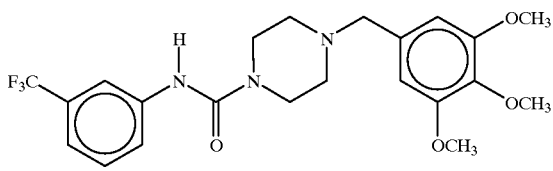

t-Boc-piperazine (8.6 g, 100 mmol) and 3,4,5-trimethoxybenzaldehyde (100 mmol) were combined with anhydrous MeOH (150 mL) and stirred until a clear solution was obtained. Acetic acid (6.0 g) was added followed by 47 g of molecular sieves (4 Å). After gently stirring for 1 hr, the mixture was chilled in ice and NaCNBH$_4$ (6.1 g, 100 mmol) was added in small portions over a period of 1.5 hr with gentle stirring. Stirring was continued for 70 hr and the mixture was filtered and the filtrate was evaporated under reduced pressure. The resultant oily residue was treated with water and 10 g of NH$_4$Cl. The suspension was stirred and acidified to pH ~4 with solid KHSO$_4$. The suspension was neutralized with NaHCO$_3$ and extracted thoroughly with EtOAc. The organic layer was washed with water, dried over Na$_2$SO$_4$, and concentrated under reduced pressure to provide a semi-solid residue. The residue was triturated with anhydrous ether and the crystalline solid was filtered off and washed with cold ether. The solid was dried in air for 2 hr, then in vacuo for 2 hr to provide 8.63 g of a solid with m.p. 153–155° C. compound 1. FABMS: 367 (MH+).

A portion of the solid (7.28 g, 20 mmol) was dissolved in chilled 95% TFA/H$_2$O (50 mL). The mixture was stirred for 30 min in ice, then TFA was removed under reduced pressure. The residue was treated with water, acidified with 1N HCl to pH 3–4, and extracted with ether (3×20 mL). The aqueous layer was chilled in ice and neutralized with solid Na$_2$CO$_3$ and the pH was adjusted to 10 with 1N NaOH. The resulting solution was extracted with EtOAc (5×40 mL). The aqueous layer was saturated with NaCl and again extracted with EtOAc (2×30 mL). The combined EtOAc extracts were washed with water, brine, dried over Na$_2$SO$_4$ filtered and evaporated under reduced pressure to furnish 2. Compound 2 was dried overnight in a vacuum desiccator, dissolved in anhydrous DMF (35 mL) and chilled in ice. To the chilled stirring solution of 2, was added portionwise a solution of 3-trifluoromethylisocyanate (3.74 g, 20 mmol) in dry DMF (15 mL). The reaction was monitored for both the consumption of isocyanate and the consumption of free amine. After each addition of isocyanate the reaction mixture was stirred for 20 min before aliquot removal for TLC. After the final addition, the reaction mixture was allowed to stir overnight. DMF was removed under reduced pressure and the residue was treated with 10% Na$_2$CO$_3$ solution (50 mL). The resulting suspension was stirred for 10 min and then extracted with EtOAc (5×50 mL). The organic layer was washed with water (2×25 mL), brine, dried over Na$_2$SO$_4$ and evaporated under reduced pressure. The residue was dissolved in ether and kept for several hours during which time a crystalline mass separated out, which was filtered off, washed with cold ether and dried in air. Additional drying was carried out with a vacuum desiccator overnight to provide the product compound 3, 850–0277 (7.5 g, m.p. 79–82° C.). Spectral data was consistent with the proposed structure.

1.2 Synthesis of 50-0231

This example illustrates the synthesis of calcitonin mimetic 50-0231 from commercially available starting materials using the schemes outlined above in section 1.1.

Briefly, t-Boc-piperazine (8.6 g, 100 mmol) and vanillin acetate (100 mmol) are combined with anhydrous MeOH (150 mL) and stirred until a clear solution is obtained. Acetic acid (6.0 g) is added followed by 47 g of molecular sieves (4 Å). After gentle stirring for 1 hr, the mixture is chilled in ice and NaCNBH$_4$ (6.1 g, 100 mmol) is added in small portions over a period of 1.5 hr with gentle stirring. Stirring is continued for 70 hr and the mixture is filtered and the filtrate is evaporated under reduced pressure. The resultant oily residue is treated with water and 10 g of NH$_4$Cl. The suspension is stirred and acidified to pH ~4 with solid KHSO$_4$. The suspension is neutralized with NaHCO$_3$ and extracted thoroughly with EtOAc. The organic layer is washed with water, dried over Na$_2$SO$_4$, and concentrated under reduced pressure to provide a semi-solid residue. The residue is titrated with anhydrous ether and the crystalline solid is filtered off and washed with cold ether. The solid is dried in air for 2 hr, then in vacuo for 2 hr.

A portion of the solid (20 mmol) is dissolved in chilled 95% TFA/H$_2$O (50 mL). The mixture is stirred for 30 min in ice, then TFA is removed under reduced pressure. The residue is treated with water, acidified with 1N HCl to pH 3–4, and extracted with ether (3×20 mL). The aqueous layer is chilled in ice and neutralized with solid Na$_2$CO$_3$ and the pH is adjusted to 10 with 1N NaOH. The resulting solution is extracted with EtOAc (5×40 mL). The aqueous layer is saturated with NaCl and again extracted with EtOAc (2×30 mL). The combined EtOAc extracts are washed with water, brine, dried over Na$_2$SO$_4$, filtered and evaporated under reduced pressure. The compound is dried overnight in a vacuum desiccator, dissolved in anhydrous DMF (35 mL) and chilled in ice. To the chilled stirring solution is added portionwise a solution of 3-trifluoromethylisocyanate (3.74 g, 20 mmol) in dry DMF (15 mL). The reaction is monitored for both the consumption of isocyanate and the consumption of free amine. After each addition of isocyanate the reaction mixture is stirred for 20 min before aliquot removal for TLC. After the final addition, the reaction mixture is allowed to stir overnight. DMF is removed under reduced pressure and the residue is treated with 10% Na$_2$CO$_3$ solution (50 mL). The resulting suspension is stirred for 10 min and then extracted with EtOAc (5×50 mL). The organic layer is washed with water (2×25 mL), brine, dried over Na$_2$SO$_4$ and evaporated under reduced pressure. The residue is dissolved in ether and kept for several hours during which time a crystalline mass separates out, which is filtered off, washed with cold ether and dried in air. Additional drying is carried out with a vacuum desiccator overnight to provide the product compound 50-0231:

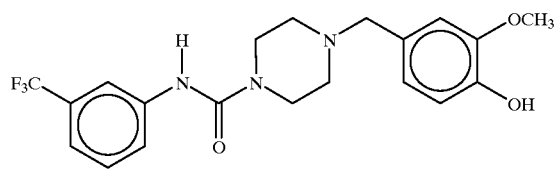

Example 2

This example describes the preparation of calcitonin mimetics in which a piperazine is substituted with two benzylic groups.

Briefly, t-Boc-piperazine is alkylated with a first substituted aryl aldehyde using the reductive alkylation conditions described above. The product is then deprotected and alkylated with a second substituted aryl aldehyde using conditions similar to those for the first reductive alkylation. Compounds which can be prepared using this general procedure as well as that of Example 1 are depicted in the table below along with activity as measured in the CRE-Luciferase assay described below.

Receptor-positive and -negative cell lines were maintained by serial passage in growth medium (DMEM supplemented with 10% heat-inactivated fetal calf serum (HI-FCS), 2 mM L-glutamine, 1 mM sodium pyruvate, 250 nM MTX, and 1 mg/mL G418). On the day prior to assay, cells

TABLE 1

Calcitonin Mimetics and Activity

| Compound | Structure | $EC_{50}$ ($\mu$g/mL) |
|---|---|---|
| 850-0231[1] | 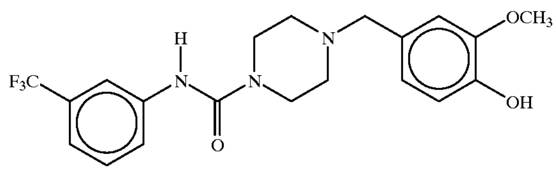 | 25–50 |
| 850-0293 | 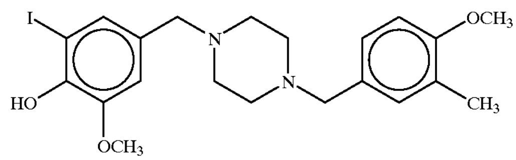 | 25–50 |
| 850-1085 | 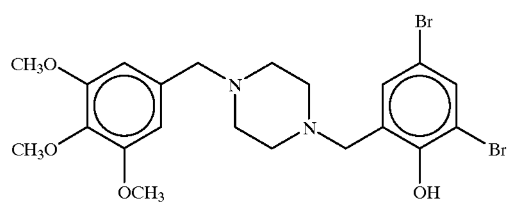 | 35.5 |
| 850-0221 | 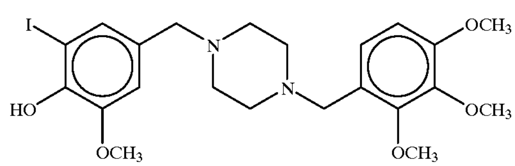 | 154 |
| 50-2013 | 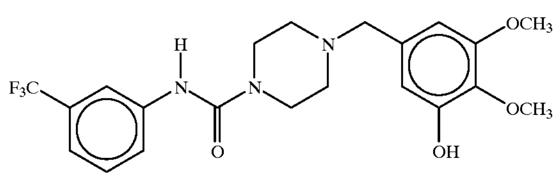 | 19 |
| 850-2346 | 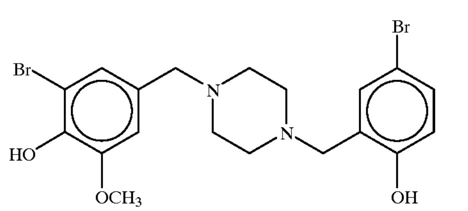 | 100 |

[1]Compound 850-0231 is also referred to herein as compound 50-0231, compound 850-0276, and compound 50-0276.

Example 3

This example provides both in vitro and ex vivo assays which can be used to evaluate compounds described herein for their use in therapeutic methods as well as their use as standards in binding assays for development of other calcitonin mimetics.

3.1 Assay for Calcitonin Mimetic Activity: A CRE-Luciferase Assay Method for Calcitonin Mimetics were trypsinized, adjusted to $2\times10^5$ cells/mL in growth medium, plated in opaque white Dynatech Microlite microtiter tissue culture plates at 100 $\mu$L/well ($2\times10^4$ cells), and grown overnight to confluence (37° C., 5% $CO_2$ atmosphere).

Test substances were prepared in DMSO at 100 times the final desired assay concentration. Induction was initiated by adding 100 $\mu$L/well test substance diluted 1:100 or 1:1000

(only first round screening extracts were diluted 1:100) in assay medium (DMEM supplemented with 10% HI-FCS, 2 mM L-glutamine, 1 mM sodium pyruvate and 20 mM Hepes, pH 7.25). Controls were included on each plate: untreated wells (basal), 25 mM forskolin, and 100 nM human calcitonin. For test substances prepared in DMSO, an equal concentration of DMSO was included in control wells (not to exceed a final assay concentration of 2% DMSO, with a preferred maximum of 1%). Plates were incubated for 3 to 8 hours (4 hours preferred) at 37° C. in an atmosphere of 5% $CO_2$.

Following induction, luciferase activity was measured using a Promega luciferase assay kit (E1500) according to the assay kit protocol. Briefly, assay medium was removed and cells were washed once with phosphate buffered saline (PBS). After the wash, 25 μL of lysis buffer was added to each well, and the plates were incubated for 15 minutes at room temperature. Fifty microliters of Luciferase Assay Substrate (Promega, Corp.) was added to each well and the plates were transferred to a Labsystems Lumiscan microtiter luminometer. The amount of luminescence (relative light units, RLU) was determined by "Fastscan" following a 0.1 second/well integration of signal. Basal (uninduced) luciferase signal was subtracted from all measurements, and the luciferase signal induced by test samples was expressed as a percentage of the signal in the calcitonin and forskolin controls. Specificity of the luciferase induction for calcitonin receptor-positive cell lines was determined by comparing the percent control values in the calcitonin receptor-positive lines (Hollex-2) to those observed in the calcitonin receptor-negative cell line (KZ10-20-48/Zem 228) and in the glucagon receptor-positive cell line (KZ10-20-48/pLJ6-4-25). Samples inducing a signal over the basal level were selected for further characterization.

3.2 Calvarial Assay

Calvaria from 4-day old neonatal CD-1 mice (pregnant mice received from Charles River Laboratories, Wilmington, Mass.) were trimmed with fine-tipped scissors to leave the parietal regions, including the sagittal suture. These trimmed bones were placed singly per well into 6-well cell culture cluster plates (Costar, Pleasanton, Calif.) with 1 mL/well of growth medium (DMEM, BioWhittaker, Walkersville, Md.) with 4.5 g/L glucose, 0.29 mg/mL L-glutamine, 1 mM sodium pyruvate, 15% heat-inactivated horse serum, and antibiotics (penicillin-G 50 μg/mL, streptomycin 50 μg/mL, and neomycin 100 μg/mL), and rocked gently (RedRocker™, model PR50-115V, Hoefer, San Francisco, Calif.) at 37° C. in a 5% $CO_2$ humidified incubator for 24 hours preincubation.

Following preincubation, medium was removed and replaced with 1.5 mL/well of growth medium containing 1 nM parathyroid hormone (PTH) 1–34 (Sigma) to stimulate bone resorption. For evaluation of the ability of calcitonin mimetics to inhibit PTH induced bone resorption, mimetic compounds in DMSO were added to the growth medium at concentrations ranging from 1–400 μg/mL (final assay concentration of DMSO less than or equal to 1% ). In each experiment human calcitonin (0.02–20 nM, 0.2–2 nM preferred) was added to PTH treated bones as a positive control. Control wells that did not receive PTH, human calcitonin or calcitonin mimetic were included for determination of calcium release from untreated bones. All control wells contained a final assay concentration of DMSO equal to that present in calcitonin mimetic treated wells.

Five bones were included in each sample group. Bones were incubated for 72 hours following PTH addition to allow resorption of bone to occur. Observations were made of the general appearance, healthiness and number of cells that migrate from the calvaria during the incubation as a possible indication of possible toxicity. Calvaria to be examined histologically were transferred to glass scintillation vials containing 10 mL of 10% neutral buffered formalin. The medium was removed from the wells, and total calcium measurements were made using a Nova 7/7+7 Electrolyte Analyzer (Nova Biomedical, Waltham, Mass.) according to the manufacturer's specifications. Induction of bone resorption by PTH is seen as an increase in the concentration of calcium in the growth medium due to degradation of the bone matrix. Human calcitonin and biologically active calcitonin mimetics inhibit this bone resorptive process as demonstrated by a lowering of the calcium in growth medium as compared to bones treated with PTH alone.

3.3 Calvaria Histoloqy

To confirm the findings in the calvarial bone resorption assay employing calcium release from culture mouse calvariae, selected bones were fixed in 10% neutral buffered formalin and demineralized in 5% formic acid with 5% formalin. The bones were dehydrated through an ascending series of ethanol concentrations, infiltrated in glycol methacrylate, and embedded using a JB-4 embedding kit (PolySciences, Warrington, Pa.) (Liu et al., *J. Bone Mineral Res.* 5:973–82 (1990)). Cross sections of calvariae cut at 5 μm were obtained and stained for tartrate-resistant acid phosphatase (TRAP) activity and counterstained with methyl green and thionin for cell morphology (Liu et al., supra). Osteoclasts were identified by TRAP stain, multinucleation, large cell size, and irregular cell shape. The number of osteoclasts were counted from endocranial and ectocranial bone surfaces and expressed as number/mm perimeter. The size of all the osteoclasts counted was also measured using a Bone Morphometry program (Liu et al., supra; Bain, et al., *J. Bone Miner. Res.* 8:435–42 (1993)). This histomorphometric method demonstrated increases in the number and size of osteoclasts due to human parathyroid hormone (PTH 1–34) treatment. This PTH-induced increase was suppressed by treatment with human calcitonin.

Calcitonin mimetic compounds were evaluated in a similar fashion for their ability to suppress PTH-induced increases in osteoclast number and size. Cell toxicity (or death) was also evaluated by the appearance of pyknotic nuclei in a small number of bone cells. With an increased level of toxicity, a further increase in the number of these pyknotic nuclei, detachment of cells from bone surfaces, and losses of cytoplasmic stain and cell boundaries were observed. The osteolytic space also appeared empty.

TABLE 2

Effect of Calcitonin Mimetics on PTH-Induced Bone Resorption in Mouse Calvariae
Release of PTH Induced $Ca^{++}$

| Calcitonin Mimetic | IC50 (μg/mL) | Histology |
|---|---|---|
| 850-0277 | 50 | |
| 850-1085 | 20 | |
| 850-1561 | 15 | |
| 850-2346 | 25 | |
| 50-2013 | 15 | |
| 850-0231 | 25–50 | Inhibition of osteoclast size and number |
| 850-0293 | 25–50 | Inhibition of osteoclast size and number |

For comparative purposes, the IC50 for human calcitonin is about 0.2 to 0.5 nM.

3.4 Induction of Hypocalcemia in Rats

This assay is based on the in vivo acute effect of calcitonin on osteoclasts, which causes rapid retraction of osteoclasts from bone surface (typically within 30 minutes) and which results in decreased bone resorption. See Mills, et al., in Endocrinology 1971—Proceedings of the Third International Symposium, Taylor (ed), Heinemann Medical, London, pp. 79–88 (1972) and Singer, et al., *Clin. Endocrinol.* 5(Supp):333s–340s (1976); the disclosures of which are incorporated herein by reference. The assay method was modified from the method described by Sturtridge and Kumar, *Lancet* 545:725–6, 1968, the disclosure of which is incorporated herein by reference.

For the assay of hypocalcemic activity, weanling male Holtzman Sprague-Dawley rats (22 days old) are infused with vehicle (PBS with 1 mM HCl and 0.1% BSA), calcitonin or calcitonin mimetics through the tail vein. One hour later, blood samples are collected by orbital sinus puncture to determine serum levels of calcium. A decrease in serum calcium indicates a hypocalcemic response. The hypocalcemic response is dose-dependent as determined using salmon calcitonin (0.5, 2.5, 5, 50 and 100 ng/rat) in this model.

3.5 Inhibition of PTH-Induced Hypercalcemia in TPTX Rats

Continuous PTH infusion is associated with extensive destruction and severe hypercalcemia in thyroparathyroidectomized (TPTX) rats. See Thompson et al., *Proc. Natl. Acad. Sci. USA* 85:5673–5677 (1988), incorporated herein by reference. An animal model has been successfully established. See Liu et al., *J. Bone Mineral Res.* 11(Suppl. 1):S206 (1996), incorporated herein by reference.

For in vivo assay, male Sprague-Dawley rats (weighing about 150 g) are thyroparathyroidectomized and the success of surgery is determined by measuring the levels of serum calcium. Animals which are successfully operated on (serum calcium levels less than 8 mg/dl) are maintained on a low calcium diet (0.02% Ca and 0.6% P, ICN special diet) and infused s.c. with vehicle (PBS with 1 mM HCl and 0.1% BSA), PTH (75 $\mu$g human PTH 1–34/kg body weight/day), PTH+calcitonin (salmon calcitonin 50 U/kg body weight/day), or PTH+calcitonin mimetic via Alzet osmotic minipumps (Model 1003D, Alza Corp., Palo Alto, Calif. U.S.A.). Two days after infusion, animals are sacrificed and blood samples are collected to determine if the hypercalcemic response induced by PTH is inhibited by co-administration of calcitonin or calcitonin mimetic.

Additionally, tibial and kidney samples are collected to determine osteoclastic bone resorption and nephrocalcinosis, respectively, and to confirm the findings in serum chemistry. Severe hypercalcemia induced by PTH has been shown to be accompanied by increases in the number and size of osteoclasts, extensive bone destruction, and calcification in kidneys (nephrocalcinosis) following only two days of treatment (see, Liu, et al., supra.). Serum, bone and kidney changes were attenuated by co-administration of CT.

3.6 Bone Loss Induced by Combined Ovariectomy and Immobilization in Rats

Estrogen deficiency and immobilization both induce bone loss in humans and in experimental animals. The combined effects cause severe osteopenia. See, Strachan et al., *J. Bone Mineral Res.* 11(Suppl. 1):S456 (1996), incorporated herein by reference. A few studies have also shown that calcitonin is effective at reducing bone loss associated with combined ovariectomy and immobilization. See, Hayashi et al., *Bone* 10:25–28 (1989) and McSheehy et al., *Bone* 16:435–444 (1995), the disclosures of each being incorporated herein by reference. Slightly modified procedures were recently used to reproduce those results and demonstrate that calcitonin is very effective at reducing bone loss associated with the combined surgery, when evaluated by pQCT or histomorphometry in rats (see, Strachan et al., *J. Bone Mineral Res.* 11(Suppl. 1):S456 (1996).

For induction of bone loss, 2-month old Sprague-Dawley rats (weighing about 200 g) are ovariectomized and immobilized by neurotomy of the sciatic nerve in the left hind limb. The immobilized animals are treated with vehicle (PBS with 1 mM HCl and 0.1% BSA), calcitonin (15 U/kg body weight/day),or calcitonin mimetics for 6 weeks. Calcitonin injections (15 mg/kg body weight/day) are given i.p. at 9 and 2 days prior to sacrifice. Bone histomorphometry is performed as previously described (see, Liu et al., *J. Bone Mineral Res.* 5:973–982 (1990)) to determine the effects of calcitonin and calcitonin mimetics.

3.7 Calvarial Assay to Determine Calcitonin Escape

Calvaria from 4-day old neonatal CD-1 mice (pregnant mice received from Charles River Laboratories) were trimmed with fine-tipped scissors to leave the parietal regions, including the sagittal suture. These trimmed bones were placed singly per well into 6-well culture cluster plates (Costar) with 1 mL/well of growth medium, Basel Medium (Eagle's with Earle's salts (GIBCO BRL, Gaithersburg, Md.)) containing 4.5 g/L glucose, 0.29 mg/mL L-glutamine, 1 mM sodium pyruvate, 15% heat-inactivated horse serum, antibiotics (penicillin-G 50 $\mu$g/mL, streptomycin 50 $\mu$g/mL, and neomycin 100 $\mu$g/mL) and containing 5 nM parathyroid hormone (PTH) 1–34 (Sigma), and rocked gently (RedRocker™) at 37° C. in a 5% $CO_2$ humidified incubator for 17.5 hours preincubation. The concentration of PTH was chosen to insure maximum resorption. Calvaria designated as controls were pre-incubated in media without PTH.

Following preincubation, medium was removed and replaced with 1 mL/well of growth medium, as above, containing 20 or 30 $\mu$g/mL of the calcitonin mimetic 850-0231 in DMSO (final assay concentration of DMSO less than or equal to 1%), and compared with human calcitonin (hCT) tested at 0.5, 1.0, 5.0, or 10 nM and salmon calcitonin (sCT) tested at 0.01, 0.02, 0.05, or 0.2 nM. Control wells that did not receive PTH, human or salmon calcitonin or the calcitonin mimetic were included for determination of calcium release from untreated bones. All control wells contained a final assay concentration of DMSO equal to that present in the calcitonin mimetic treated wells.

Five bones were included in each sample group. Bones were incubated for a total of 98 hours. Time points were taken at 4, 8, 11, 24, 50.5, 72.5 and 98 hours. At each time point the media containing PTH was removed and fresh dilutions of compound in media were added to the calvaria. After the media was removed, total calcium measurements were made using a Nova 7/7+7 Electrolyte Analyzed (Nova Biomedical) according to the manufacturer's specifications. Induction of bone resorption by PTH is seen as an increase in the concentration of calcium in the growth medium due to degradation of the bone matrix.

Human and salmon calcitonin and biologically active calcitonin mimetics inhibit the bone resorptive process as demonstrated by a lowering of the calcium in growth medium as compared to bones treated with PTH alone. However, as seen in Table 3, the inhibitory effect of hCT and sCT was lost after approximately 24 hours and the rate of resorption follows the same slope as that of PTH alone. The calcitonin mimetic 850-0231 did not undergo this escape and continued to inhibit resorption throughout the $98^{th}$ hour at 30 $\mu$g/mL.

TABLE 3

| | Cumulative Total Calcium (mg %) | | | | | | |
|---|---|---|---|---|---|---|---|
| | 4 hours | 8 hours | 11 hours | 24 hours | 50.5 hours | 72.5 hours | 98 hours |
| PTH 5 nM | 0.56 | 1.08 | 1.50 | 3.76 | 9.28 | 13.20 | 16.20 |
| PTH 5 nM + hCT 10 nM | 0.02 | 0.02 | −0.02 | 0.98 | 4.96 | 8.24 | 12.26 |
| PTH 5 nM + sCT 0.2 nM | 0.10 | 0.18 | 0.34 | 1.76 | 6.12 | 9.88 | 13.22 |
| PTH 5 nM + 850-0231 30 μg/mL | 0.16 | 0.28 | 0.38 | 0.48 | 0.32 | 0.12 | −0.18 |

Average of 5 samples, control values were subtracted.

Visual observation of the calvaria at the final time point showed that the PTH treated calvaria had undergone obvious resorption. The human and salmon calcitonin and 850-0231 calcitonin mimetic treated calvaria have undergone less resorption, and the mimetic treated calvaria was almost identical in appearance to the untreated calavaria. Furthermore, the fact that an equal number of cells had migrated from the control and 850-0231 treated calvaria indicated that this compound is not toxic to the cells.

Figure 4A:
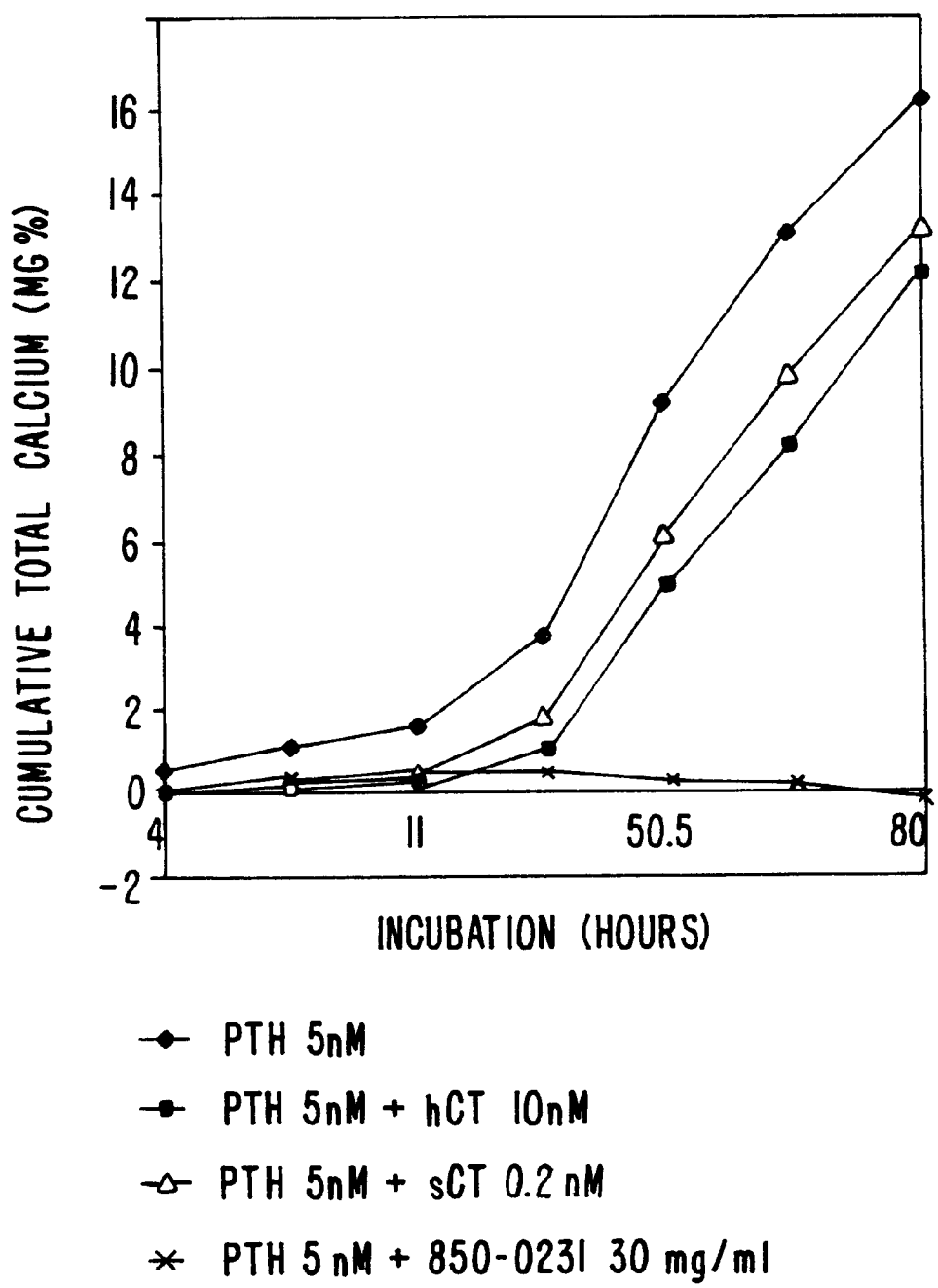
FIGS. 4A–C show graphs of cumulative total calcium (mg %) vs. incubation time (hours) for calvarial assays to determine calcitonin escape
Figure 4B:
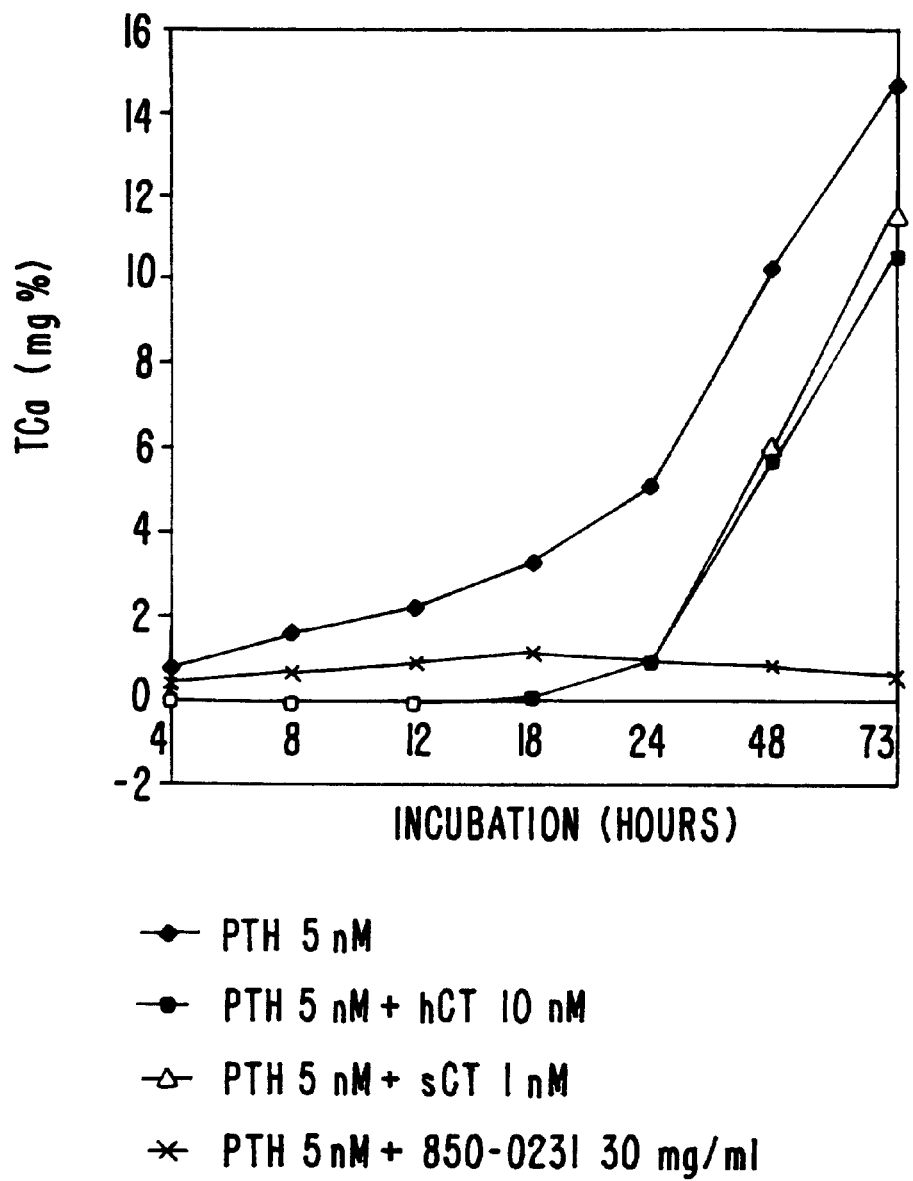
Figure 4C:
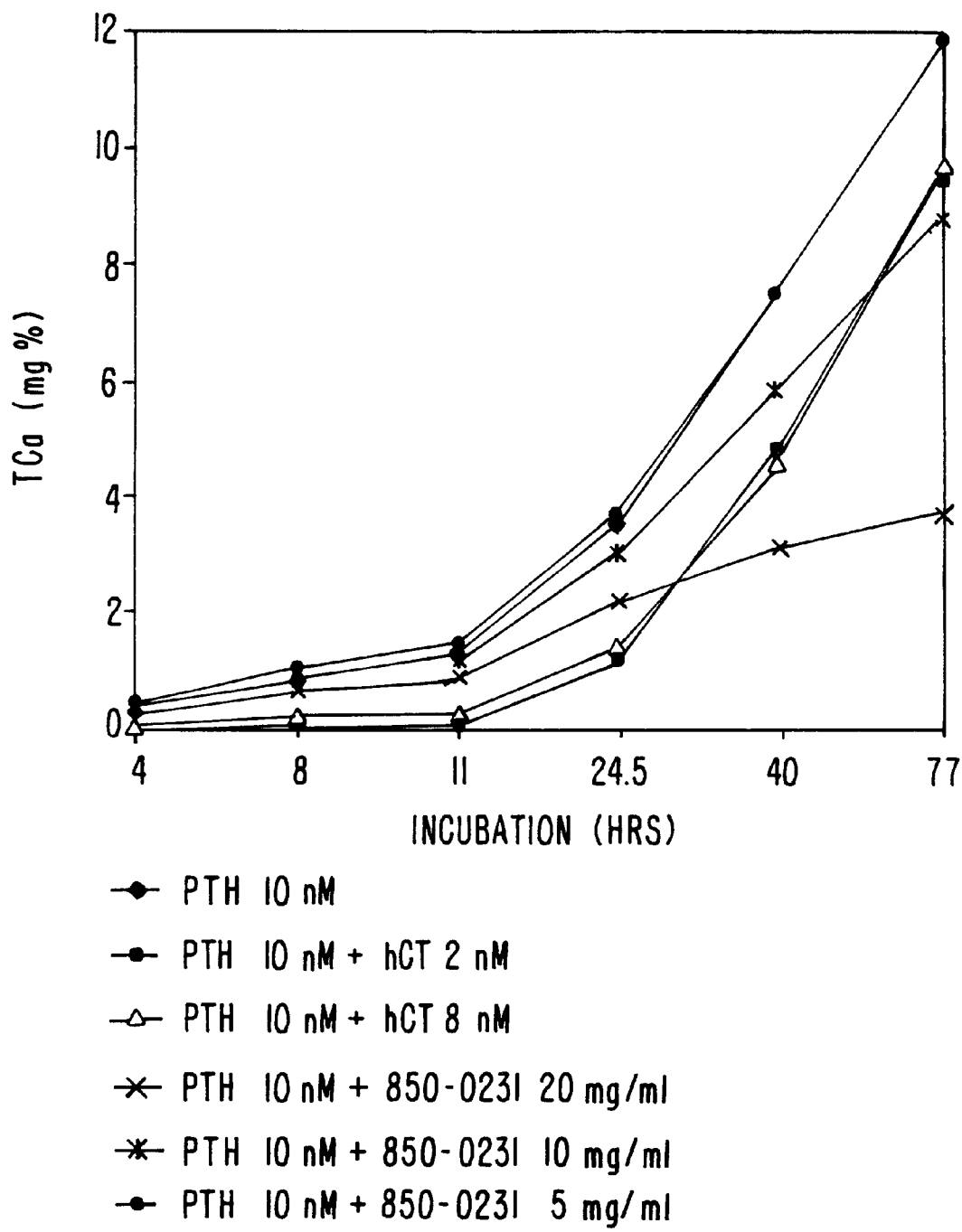

A second calvaria bone resorption/escape assay was performed as described above with time points at 4, 8, 12, 16, 24, 49 and 73 hours. Again human and salmon calcitonin lost their inhibitory effect between hours 16 and 24 and the calcitonin mimetic 850-0231 was able to continue inhibition of resorption throughout the $73^{rd}$ hour (FIG. 4). Histology was done on the PTH-treated and the 30 μg/mL calcitonin mimetic-treated calvaria. The PTH samples were almost completely resorbed while the mimetic-treated calvaria were intact and showed minimal signs of toxicity.

TABLE 4

| | Cumulative Total Calcium (mg %) | | | | | | |
|---|---|---|---|---|---|---|---|
| | 4 hours | 8 hours | 12 hours | 16 hours | 24 hours | 49 hours | 73 hours |
| PTH 5 nM | 0.74 | 1.58 | 2.18 | 3.26 | 5.04 | 10.36 | 14.68 |
| PTH 5 nM + hCT 10 nM | 0.10 | −0.04 | −0.06 | 0.12 | 0.92 | 5.70 | 10.60 |
| PTH 5 nM + sCT 1 nM | −0.02 | −0.16 | −0.20 | 0.08 | 0.92 | 6.02 | 11.56 |
| PTH 5 nM + 850-0231 30 μg/mL | 0.40 | 0.70 | 0.88 | 1.14 | 1.04 | 0.86 | 0.56 |

Average of 5 samples, control values were subtracted.

A third calvaria bone resorption/escape assay was performed as described above with the following modifications. The calcitonin mimetic was tested at 5, 10 and 20 μg/mL. PTH was used at 10 nM to insure maximal resorption, hCT was tested at 2 nM and 8 nM and sCT was not included. Calvaria were pretreated with PTH for 19.75 hours. BrdU (bromodeoxyuridine, final concentration 10 μM) was added to the growth media for the final 17.5 hours, to identify proliferating cells. The lack of toxicity of 850-0231 will be verified by quantitating the number of proliferating BudU+ cells in histological sections of the calvaria. Time points were taken at 4, 8, 11, 24.5, 48 and 77 hours. A Novo CRT 10+ electrolyte analyzer (Nova Biomedical) was used to analyze the time point samples.

At the final time point, visual observations were made and photos taken to note the extent of resorption, and migration from the calvarial cells as a measure of toxicity. Again, human calcitonin lost its inhibitory effect between hours 11 and 24 (Table 5). The calvaria treated with the mimetic at 5 and 10 μg/mL also lost inhibitory effect between 11 and 24 hours. Resorption was significantly inhibited at all time points by 20 μg/mL 850-0231, although not to the extent of the 30 μg/ml treated calvaria described above.

TABLE 5

| | Cumulative Total Calcium (mg %) | | | | | |
|---|---|---|---|---|---|---|
| | 4 hours | 8 hours | 11 hours | 24.5 hours | 48 hours | 77 hours |
| PTH 10 nM | 0.45 | 1.03 | 1.42 | 3.55 | 7.51 | 11.74 |
| PTH 10 nM + hCT 2 nM | 0.01 | 0.10 | 0.10 | 1.22 | 4.88 | 9.55 |
| PTH 10 nM + hCT 8 nM | 0.08 | 0.24 | 0.27 | 1.45 | 4.60 | 9.74 |
| PTH 10 nM + 850-0231 20 μg/mL | 0.35 | 0.70 | 0.94 | 2.23 | 3.20 | 3.78 |
| PTH 10 nM + 850-0231 10 μg/mL | 0.41 | 0.87 | 1.30 | 3.05 | 5.96 | 8.87 |
| PTH 10 nM + 850-0231 5 μg/mL | 0.47 | 1.08 | 1.49 | 3.73 | 7.54 | 11.83 |

Average of 5 samples, control values were subtracted.

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

What is claimed is:

1. A method for treating a bone-related disorder involving bone resorption, the method comprising administering to a subject suffering from such disorder an effective amount of an anti-resorptive compound of formula I:

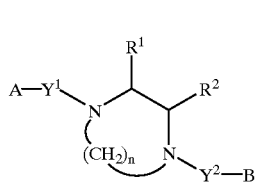

(I)

wherein A is a member independently selected from group consisting of:

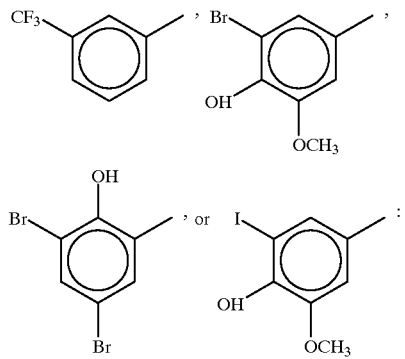

B is a member independently selected from the group consisting of aryl, substituted aryl, carbocyclic ring, substituted carbocyclic ring, heterocyclic ring, substituted heterocyclic ring, and combinations thereof, said combinations being fused or covalently linked and said substituents being selected from the group consisting of halogen, haloalkyl, hydroxy, aryloxy, benzyloxy, alkoxy, haloalkoxy, amino, monoalkylamino, dialkylamino, acyloxy, acyl, alkyl and aryl;

$R^1$ and $R^2$ are each independently selected from the group consisting of hydrogen and alkyl groups having from 1 to 6 carbon atoms, or taken together form a ring selected from the group consisting of saturated or unsaturated five-member rings, saturated or unsaturated six-member rings and saturated or unsaturated seven-member rings;

$Y^1$ and $Y^2$ are each independently a bond or a divalent radical selected from the group consisting of —CH2—, —NHC(O)—, —NRC(O)—, —NHC(S)—, —NRC(S)—, —NHC(=NH)—, —OC(O)—, —C(O)—, or —C(S)—, in which R is a lower alkyl group of from one to six carbon atoms; and n is an integer of from zero to four.

2. A method in accordance with claim 1, wherein said compound has the formula:

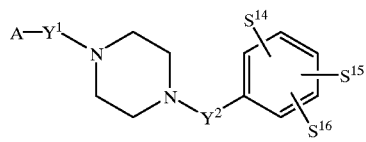

wherein, A is a member independently selected from group consisting of:

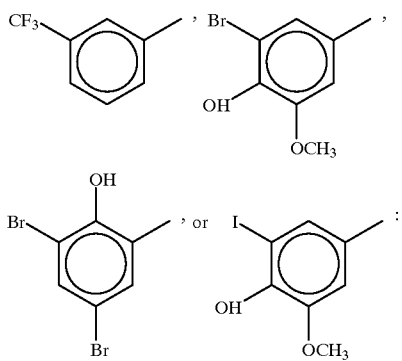

$Y^1$ and $Y^2$ are each independently a divalent radical selected from the group consisting of —CH2—, —NHC(O)—, —NRC(O)—, —NHC(S)—, —NRC(S)—, —NHC(=NH)—, —OC(O)—, —C(O)—, or —C(S)—, in which R is a lower alkyl group of from one to six carbon atoms; and $S^{14}$, $S^{15}$, and $S^{16}$ are each independently a member selected from the group consisting of hydrogen, halogen, haloalkyl, hydroxy, aryloxy, benzyloxy, alkoxy, haloalkoxy, amino, monoalkylamino, dialkylamino, acyloxy, acyl, alkyl and aryl.

3. A method in accordance with claim 2, wherein $Y^1$ is —NHC(O) or —CH2—, Y2 is —CH2—, and $S^{14}$, $S^{15}$, and $S^{16}$ are each independently members selected from the group consisting of hydrogen, halogen, haloalkyl, hydroxy, alkoxy, haloalkoxy, amino, monoalkylamino or dialkylamino.

4. A method in accordance with claim 2, wherein $S^{14}$, $S^{15}$, and $S^{16}$ are each independently members selected from the group consisting of hydrogen, halogen, trifluoromethyl, hydroxy and methoxy.

5. A method in accordance with claim 2, wherein $Y^1$ is —NHC(O) or —CH2—, Y2 is —CH2—, and $S^{14}$, $S^{15}$, and $S^{16}$ are each independently members selected from the group consisting of hydrogen, halogen, trifluoromethyl, hydroxy and methoxy.

6. A method in accordance with claim 1, wherein said bone-related disorder is selected from the group consisting of osteoporosis, Paget's disease, hyperpara-thyroidism, osteomalacia, periodontal applications (bone loss), hypercalcemia of malignancy and hypercalcemia of infancy.

7. A method of inhibiting bone resorption, the method comprising administrating to a subject in need of such inhibition an effective amount of a compound of formula I:

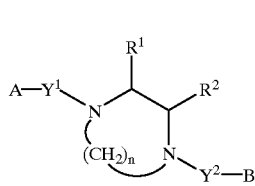

wherein A is a member independently selected from group consisting of:

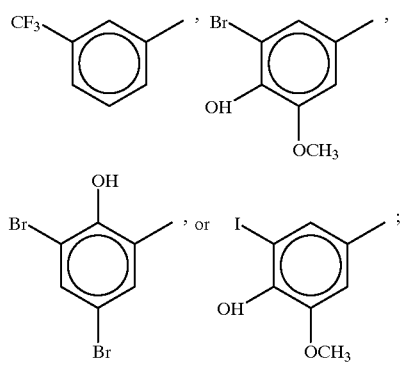

B is a member independently selected from the group consisting of aryl, substituted aryl, carbocyclic ring, substituted carbocyclic ring, heterocyclic ring, substituted heterocyclic ring, and combinations thereof, said combinations being fused or covalently linked and said substituents being selected from the group consisting of halogen, haloalkyl, hydroxy, aryloxy, benzyloxy, alkoxy, haloalkoxy, amino, monoalkylamino, dialkylamino, acyloxy, acyl, alkyl and aryl;

$R^1$ and $R^2$ are each independently selected from the group consisting of hydrogen and alkyl groups having from 1 to 6 carbon atoms, or taken together form a ring selected from the group consisting of saturated or unsaturated five-member rings, saturated or unsaturated six-member rings, saturated or unsaturated six-member rings and saturated or unsaturated seven-member rings;

$Y^1$ and $Y^2$ are each independently a bond or a divalent radical selected from the group consisting of —CH2—, —NHC(O)—, —NRC(O)—, —NHC(S)—, —NRC(S)—, —NHC(=NH)—, —OC(O)—, —C(O)—, and —C(S)—, in which R is a lower alkyl group of from one to six carbon atoms; and n is an integer of from zero to four.

8. A method in accordance with claim 7, wherein said compound has the formula:

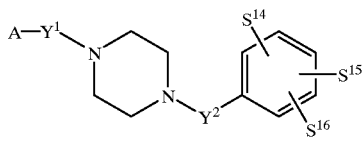

wherein, A is a member independently selected from the group consisting of

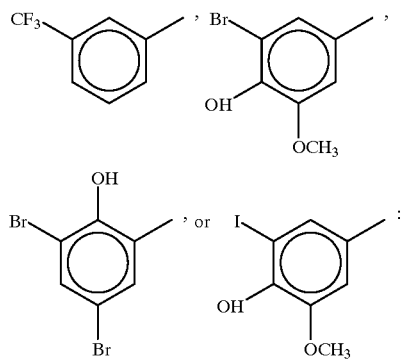

$Y^1$ and $Y^2$ are each independently a bond or a divalent radical selected from the group consisting of —CH2—, —NHC(O)—, —NRC(O)—, —NHC(S)—, —NRC(S)—, —NHC(=NH)—, —OC(O)—, —C(O)—, and —C(S)—, in which R is a lower alkyl group of from one to six carbon atoms; and $S^{14}$, $S^{15}$, and $S^{16}$ are each independently a member selected from the group consisting of hydrogen, halogen, haloalkyl, hydroxy, aryloxy, benzyloxy, alkoxy, haloalkoxy, amino, monoalkylamino, dialkylamino, acyloxy, acyl, alkyl and aryl.

9. A method in accordance with claim 8, wherein $Y^1$ is —CH2—, —NHC(O)—, or —CH2—, Y2 is —CH2—, and $S^{14}$, $S^{15}$, and $S^{16}$ are each independently members selected from the group consisting of hydrogen, halogen, haloalkyl, hydroxy, alkoxy, haloalkoxy, amino, monoalkylamino or dialkylamino.

10. A method in accordance with claim 8, wherein $S^{14}$, $S^{15}$, and $S^{16}$ are each independently members selected from the group consisting of hydrogen, halogen, trifluoromethyl, hydroxy and methoxy.

11. A method in accordance with claim 8, wherein $Y^1$ is —NHC(O)—, or —CH2—, Y2 is —CH2—, and $S^{14}$, $S^{15}$, and $S^{16}$ are each independently members selected from the group consisting of hydrogen, halogen, trifluoromethyl, hydroxy and methoxy.

* * * * *